(12) United States Patent
Wodlinger et al.

(10) Patent No.: US 12,263,041 B2
(45) Date of Patent: Apr. 1, 2025

(54) SIGNAL PROCESSING PATHWAY FOR AN ULTRASONIC IMAGING DEVICE

(71) Applicant: EXACT IMAGING INC., Ontario (CA)

(72) Inventors: Brian C. Wodlinger, Ontario (CA); Jerrold Wen, Ontario (CA); Zahra Torbatian, Ontario (CA); Simpson Lam, Ontario (CA)

(73) Assignee: EXACT IMAGING INC., Ontario (CA)

( * ) Notice: Subject to any disclaimer, the term of this patent is extended or adjusted under 35 U.S.C. 154(b) by 358 days.

(21) Appl. No.: 16/338,113

(22) PCT Filed: Sep. 29, 2017

(86) PCT No.: PCT/CA2017/051155
§ 371 (c)(1),
(2) Date: Mar. 29, 2019

(87) PCT Pub. No.: WO2018/058248
PCT Pub. Date: Apr. 5, 2018

(65) Prior Publication Data
US 2020/0022681 A1    Jan. 23, 2020

Related U.S. Application Data

(60) Provisional application No. 62/401,350, filed on Sep. 29, 2016.

(51) Int. Cl.
*A61B 8/00* (2006.01)
*A61B 8/08* (2006.01)
*G01S 7/52* (2006.01)

(52) U.S. Cl.
CPC ............. *A61B 8/54* (2013.01); *A61B 8/085* (2013.01); *A61B 8/4477* (2013.01);
(Continued)

(58) Field of Classification Search
CPC ......... A61B 8/54; A61B 8/085; A61B 8/4477; A61B 8/4488; A61B 8/5269; A61B 8/56;
(Continued)

(56) References Cited

U.S. PATENT DOCUMENTS 5,369,624 A    11/1994 Fukukita et al.
5,388,079 A    2/1995 Kim et al.
(Continued)

FOREIGN PATENT DOCUMENTS

CN    103731166 A    4/2014
CN    103731166 B    12/2015
(Continued)

OTHER PUBLICATIONS

The Journal of Urology vol. 187, No. 4S, "Ultra High-Resolution Transrectal Ultrasound: a Novel Technique for Enhanced Prostate Cancer Imaging", Published Apr. 1, 2012 (Year: 2012).*
(Continued)

*Primary Examiner* — Yi-Shan Yang
*Assistant Examiner* — Nicholas A Robinson
(74) *Attorney, Agent, or Firm* — Tarolli, Sundheim, Covell & Tummino LLP

(57) ABSTRACT

A signal processing pathway for an ultrasonic imaging device is provided. The signal processing pathway is configured to operate in a frequency range of 1 MHz to 40 MHz inclusive and a voltage range of −80 V to +80 V inclusive.

15 Claims, 28 Drawing Sheets

(52) U.S. Cl.
CPC .......... *A61B 8/4488* (2013.01); *A61B 8/5269*
(2013.01); *A61B 8/56* (2013.01); *G01S*
*7/52095* (2013.01)

(58) Field of Classification Search
CPC ............. G01S 7/52095; G01S 15/8952; G01S
15/8956; G01S 15/8915; G01S 7/52082
See application file for complete search history.

(56) References Cited

U.S. PATENT DOCUMENTS

| | | | |
|---|---|---|---|
| 5,544,128 | A | 8/1996 | Kim et al. |
| 5,581,517 | A | 12/1996 | Gee et al. |
| 5,675,554 | A | 10/1997 | Cole et al. |
| 5,696,737 | A | 12/1997 | Hossack et al. |
| 5,895,855 | A | 4/1999 | Ishikawa et al. |
| 6,110,116 | A | 8/2000 | Wright et al. |
| 6,494,839 | B1 | 12/2002 | Averkiou |
| 6,540,700 | B1 * | 4/2003 | Fujimoto ............... A61B 8/085 601/3 |
| 7,901,358 | B2 | 3/2011 | Mehi et al. |
| 8,241,217 | B2 | 8/2012 | Chiang et al. |
| 8,317,706 | B2 | 11/2012 | Wegener |
| 8,397,574 | B2 | 3/2013 | Tanaka et al. |
| 8,641,624 | B2 | 2/2014 | Sabata |
| 8,723,399 | B2 | 5/2014 | Sammoura et al. |
| 8,834,375 | B2 | 9/2014 | Hongou et al. |
| 8,876,715 | B2 | 11/2014 | Haider et al. |
| 8,926,518 | B2 | 1/2015 | Culjat et al. |
| 9,179,891 | B2 | 11/2015 | Sasady |
| 9,244,161 | B2 | 1/2016 | Hsia et al. |
| 9,295,444 | B2 | 3/2016 | Schwartz et al. |
| 2001/0007940 | A1 | 7/2001 | Tu et al. |
| 2003/0158480 | A1 * | 8/2003 | Tornes ................... A61B 90/39 600/437 |
| 2004/0158435 | A1 * | 8/2004 | Slates ................ G05B 23/0235 702/185 |
| 2004/0173541 | A1 * | 9/2004 | Kurihara ............... B06B 1/0253 210/748.03 |
| 2007/0073154 | A1 | 3/2007 | Karasawa |
| 2007/0232924 | A1 | 10/2007 | Karasawa |
| 2007/0239001 | A1 * | 10/2007 | Mehi .................... G01S 7/52095 600/437 |
| 2008/0042519 | A1 | 2/2008 | Marshall et al. |
| 2008/0294046 | A1 | 11/2008 | Chiang et al. |
| 2011/0034209 | A1 * | 2/2011 | Rubinsky ............... G16H 30/20 455/556.1 |
| 2011/0034806 | A1 * | 2/2011 | Hartov ................. A61B 8/4411 600/443 |
| 2011/0245677 | A1 * | 10/2011 | Sato .......................... A61B 8/54 600/447 |
| 2012/0095343 | A1 * | 4/2012 | Smith ....................... A61B 8/58 600/447 |
| 2012/0249210 | A1 * | 10/2012 | Shimizu .............. G01S 7/52017 327/333 |
| 2012/0316443 | A1 * | 12/2012 | Katou ................... G01S 7/5208 600/447 |
| 2013/0072800 | A1 * | 3/2013 | Lee .......................... A61B 8/56 600/447 |
| 2013/0128690 | A1 | 5/2013 | Gopalan et al. |
| 2013/0245451 | A1 * | 9/2013 | Mochizuki ........... A61B 8/4477 600/459 |
| 2013/0253325 | A1 | 9/2013 | Call et al. |
| 2014/0121524 | A1 | 5/2014 | Chiang et al. |
| 2014/0180105 | A1 | 6/2014 | Hancock et al. |
| 2014/0269198 | A1 | 9/2014 | Ray et al. |
| 2014/0288428 | A1 * | 9/2014 | Rothberg ............ G01S 7/52034 600/447 |
| 2014/0343429 | A1 * | 11/2014 | Jensen .................. A61B 8/4444 600/443 |
| 2015/0009185 | A1 * | 1/2015 | Shi .......................... G06F 3/043 345/177 |
| 2015/0029818 | A1 * | 1/2015 | Endo .................... G01S 15/8915 367/7 |
| 2015/0080724 | A1 * | 3/2015 | Rothberg ................. A61B 8/14 600/439 |
| 2015/0080725 | A1 | 3/2015 | Wegner |
| 2015/0097468 | A1 * | 4/2015 | Hajati ................ H10N 30/1071 310/334 |
| 2015/0112181 | A1 | 4/2015 | Yoon et al. |
| 2015/0165479 | A1 | 6/2015 | Lasiter et al. |
| 2016/0058417 | A1 | 3/2016 | Kiyose et al. |
| 2016/0074016 | A1 | 3/2016 | Park et al. |
| 2016/0157818 | A1 | 6/2016 | Cho |
| 2016/0349367 | A1 * | 12/2016 | Duncan ................. A61B 8/5207 |

FOREIGN PATENT DOCUMENTS

| | | |
|---|---|---|
| JP | 2007-29198 A | 2/2007 |
| JP | 2009-514600 A | 4/2009 |
| JP | 2012-209763 A | 10/2012 |
| WO | 2007056104 A2 | 5/2007 |
| WO | 2011054597 A1 | 5/2011 |
| WO | 2015134816 A1 | 9/2015 |
| WO | WO-2016083985 A1 * | 6/2016 ........... A61B 8/4254 |

OTHER PUBLICATIONS

Hu et al: Ultrasonics, Development of a 64 channel ultrasonic high frequency linear array imaging system, Dec. 2011, 51 (8): 953-959.
Fabian, et al: Development of a Parallel Acquisition System for Ultrasound Research, 9 pages.
Chernyakova et al: Fourier-Domain Beamforming: The Path to Compressed Ultrasound Imaging, Aug. 2014, vol. 61, No. 8, 1252-1267.
LAY: Design and Manufacture of a High-Frequency Annular Array Ultrasound System for Medical Imaging, May 2011, 158 pages.
Ali et al: Texas Instruments, Signal Processing Overview of Ultrasound Systems for Medical Imaging, White Paper, Nov. 2008, 1-27 pages.
Hu et al: IEEE Transactions; Development of a Real-Time, High-Frequency Ultrasound Digital Beamformer for High-Frequency Linear Array Transducers, Feb. 2006, vol. 53, No. 2.
Written Opinion of the International Searching Authority, International Application No. PCT/CA2017/051155, dated Jan. 8, 2018, 4 pages.
International Search Report, International Application No. PCT/CA2017/051155, dated Jan. 8, 2018, 5 pages.
Chinese First Office Action issued in connection with corresponding Chinese Application No. 201780059704.8 dated Aug. 24, 2021, with English Translation.
Chinese Second Office Action issued in connection with corresponding Chinese Application No. 201780059704.8 dated Mar. 24, 2022.
EPO Communication issued in connection with corresponding EP Application No. 17854297.3-1206/3518780 dated May 29, 2020.
EPO Communication issued in connection with corresponding EP Application No. 17854297.3-1206 pursuant to Art. 94 (3) dated Mar. 7, 2022.
Japanese First Office Action issued in connection with corresponding JP Application No. 2019-517964, with English translation.
Decision of Rejection and Office Action Summary in English issued in connection with Japanese Patent Application No. 2019-517964.

* cited by examiner

SIGNAL PROCESSING PATHWAY FOR AN ULTRASONIC IMAGING DEVICE

CROSS-REFERENCE TO RELATED APPLICATIONS

This application is the National Stage of International Patent Application No. PCT/CA2017/051155, filed Sep. 29, 2017, which claims priority from U.S. Patent Application No. 62/401,350, filed Sep. 29, 2016, the disclosures of each of which are incorporated herein by reference in their entireties for any and all purposes.

TECHNICAL FIELD

The field is in ultrasonic imaging devices.

BACKGROUND

This invention relates to ultrasound diagnostic imaging systems.

SUMMARY

Ultrasound imaging systems are typically designed for ultrasonic transducer arrays over a range of frequencies and voltage. Ultrasound imaging systems rely on the transmission of ultrasound waves (sound waves greater than 1 MHz) through the body tissue to form an image. The frequency of the ultrasound wave is proportional to the resolution of the image, i.e., higher frequencies allow higher resolutions. However, higher frequency waves are attenuated more in tissue and do not penetrate as deep in the body.

Various frequencies are useful for balancing resolution (higher frequencies) with field of view (lower frequencies). Conventional ultrasound imaging devices allow for a frequency range from 1 MHz up to 15 MHz. For example, a 3.5 MHz transducer may be used to image deep abdominal structures such as the bladder and kidney (up to 30 cm from the skin surface), while a 6.5 MHz transrectal transducer may be used to image the prostate (up to 6 cm from the rectal wall).

Newer micro-ultrasound devices used for pre-clinical (small animal) imaging allow a frequency range from 15 MHz to 50 MHz. These systems allow greater resolutions down to 30 μm, but field of view is limited to about 3 cm or less.

A recent pilot study suggests that using a 21 MHz ultra-high resolution transrectal transducer to provide a detailed view of the microscopic structures (<1 mm) within the prostate may be beneficial in the diagnosis of prostate cancer. This invention allows the improved resolution of these small animal imaging systems in an ultrasound imaging device that can also be used for general ultrasound imaging of the human body.

In an aspect, there is provided an ultrasound diagnostic imaging system that allows the imaging of large organs in the human body (about 30 cm, such as the kidney) and small organs (about 3 cm, such as the prostate) at ultra-high resolution (down to 30 μm) using a single signal processing pathway.

In an aspect, there is provided an ultrasound diagnostic imaging system which supports a range of transducer frequencies and voltage levels.

In another aspect, there is provided a system and method for using a single signal pathway for a variety of ultrasonic transducer arrays. The signal pathway described herein is capable of being used with ultrasonic transducer arrays with a range of center frequencies from 1 MHz to 40 MHz without the need to replace system boards in the ultrasound imaging device.

In an example embodiment, a signal processing pathway for an ultrasonic imaging device is provided. The signal processing pathway has a transmit pathway configured to transmit a signal to an ultrasonic transducer array. The signal processing pathway also has a receive pathway configured to receive a received signal from the ultrasonic transducer array. The signal processing pathway also has a control pathway for controlling the transmission of the signal and a reception of the received signal. The transmit pathway, receive pathway, and control pathway are configured to operate in a frequency range of 1 MHz to 40 MHz inclusive and a voltage range of −80V to +80V inclusive.

In another example embodiment, a signal processing pathway for an ultrasonic imaging device is provided. The signal processing pathway includes a channel board configured to transmit a signal to and receive a signal from an ultrasonic transducer array. The signal processing pathway also includes a beamformer control board configured to control the channel board. The channel board and beamformer control board are configured to operate in a frequency range of 1 MHz to 40 MHz inclusive and a voltage range of −80V to +80V inclusive.

Figure 1:
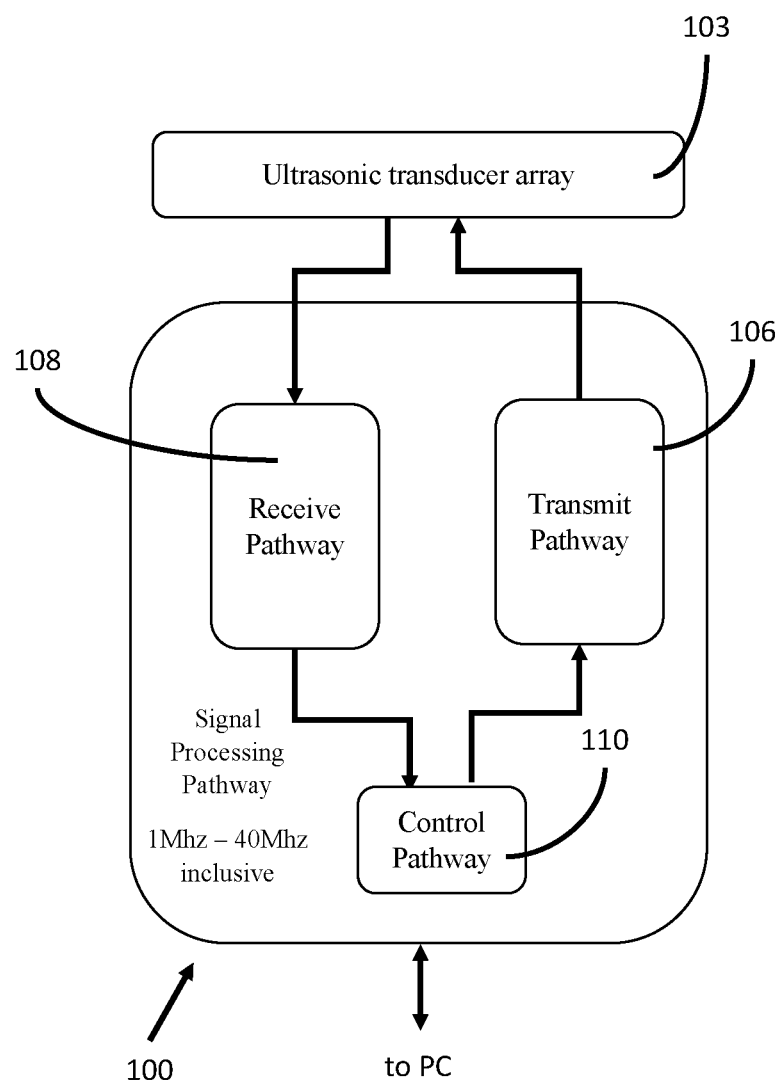
FIG. 1 (SHEET 1 of 28 SHEETS) is a block diagram of an embodiment of a signal processing pathway for an ultrasonic imaging device.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted.

Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, but well-understood, elements that are useful or necessary in commercially feasible embodiments are often not depicted to provide a less obstructed view of the embodiments of the present disclosure.

LISTING OF REFERENCE NUMERALS USED IN THE DRAWINGS 100 signal processing pathway
1000 ultrasonic imaging device
103 Ultrasonic transducer array
102 channel board
104 beamformer control board
106 Transmit (Tx) Pathway
108 Receive (Rx) Pathway
110 Control Pathway
200 Transmit (Tx) Beamformer
202 Pulser
204 Receive (Rx) Beamformer
206 Analog/Digital Converter (ADC)
208 Variable Gain Amplifier (VGA)
210 Anti-aliasing Filter (AAF)
212 Low noise Amplifier (LNA)

214 T/R Switch
216 Analog Front End (AFE)
300 Transducer element multiplexer
400 Transducer switch board
700 21 Mhz UHR-TRUS
702 6.5 Mhz TRUS
704 3.5 Mhz Abdominal

DETAILED DESCRIPTION OF THE EXEMPLARY EMBODIMENTS

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the invention is defined by the claims. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (configurations, examples, alterations, modifications, options, variations, embodiments and any equivalent thereof) are described regarding the drawings. It should be understood that the invention is limited to the subject matter provided by the claims, and that the invention is not limited to the particular aspects depicted and described.

A skilled person understands that the transmit, receive, and control pathways are signal processing pathways in an electronic circuit comprised of analog and/or digital electronic components. The electronic components may be integrated circuits, FPGAs, ASICs, and other known analog and/or digital electronic components. It is understood that an FPGA, ASIC, and other electronic components may be interchangeable. And, that the components may operate under the control of or in cooperation with software.

A skilled person would understand that an ultrasound transducer array is comprised of an array of ultrasound elements. Ultrasound transducer array is equivalent to ultrasound transducer element array. Also, a skilled person understands that an ultrasound probe comprises an ultrasound transducer array.

Referring now to FIG. 1, a signal processing pathway 100 for an ultrasonic imaging device 1000 is depicted. The signal processing pathway 100 is configured to transmit, receive, process, and control signals to and from a connected ultrasonic transducer array 103.

The signal processing pathway 100 of FIG. 1 has a transmit pathway 106, a receive pathway 108, and a control pathway 110. The signal processing pathway 100 is configured to operate in a frequency range of 1 MHz to 40 MHz inclusive and a voltage range of −80V to +80V inclusive.

The transmit pathway 106 of the signal processing pathway 100 is configured to prepare and transmit a signal, at least in part, to the ultrasonic transducer array 103. This can include, but is not limited to, beamforming (at least in part) the transmit signal, converting the transmit signal from a digital to an analog format, and pulsing the transmit signal to the ultrasonic transducer array 103

The receive pathway 108 of the signal processing pathway 100 is configured to receive a signal from the ultrasonic transducer array 103 and prepare the signal for transmission to the data processing device. This can include, but is not limited to, filtering the received signal, amplifying the received signal, removing noise from the received signal, beamforming (at least in part) the received signal, and digitizing the received signal.

The control pathway 110 of the signal processing pathway 100 is configured to control the transmit pathway 106 and the receive pathway 108. For instance, the control pathway 110 may be configured to direct the signal pathway to transmit a signal through the transmit pathway 106 or to receive a signal from the receive pathway 108. The control pathway may also direct the transmit beamformer and the receive beamformer to form, at least in part, the transmitted signal or the received signal respectively.

In the example depicted in FIG. 1, the signal processing pathway 100 is communicatively connected to an ultrasonic transducer array 103. The ultrasonic transducer array is configured to transmit and receive ultrasonic signals, at least in part, in a 1 MHz to 40 MHz range.

In some embodiments, the signal processing pathway 100 is configured to operate with commercially available ultrasonic transducer arrays. Examples of commercially available ultrasonic transducer arrays include, but are not limited to the FUJIFILM VISUALSONICS MX ULTRA-HIGH FREQUENCY LINEAR ARRAY TRANSDUCERS, a sidefire ultra-high resolution transrectal ultrasound transducer array, an endfire transrectal ultrasound transducer array, and a curved linear abdominal transducer array.

A skilled person, however, would understand that the signal processing pathway 100 may also be used with other types of ultrasonic transducer arrays. For example, the signal processing pathway 100 may also be configured to operate with phased transducer arrays, 2D array transducers, and 1.5D array transducers, among others. Furthermore, the signal processing pathway 100 may also be used with custom or proprietary ultrasonic transducer arrays.

The signal processing pathway 100 is configured to transmit, receive, and process signals from an ultrasonic transducer array that operates, in whole or in part, in a 1 MHz to 40 MHz range inclusive. In an example embodiment, a signal processing pathway 100 is configured to operate with ultrasonic transducer arrays 103 that are configured to scan using low frequency (centered around 3.5 MHz), medium frequency (centered around 6.5 MHz), and ultra-high frequency (centered around 21 MHZ or higher) ultrasound signals.

The ability to transmit, receive, and process signals in the frequency range of 1 MHz to 40 MHz allows the same signal processing pathway 100 to be used for scanning both large and small objects in a human body. That is, an ultrasonic imaging device having the presently disclosed signal processing pathway would be usable with a variety of ultrasonic transducer arrays without the need to replace system boards of the ultrasonic imaging device.

For example, the same signal pathway 100 can be used to scan both the kidneys in the abdominal cavity of a human and structures within a human prostate. Examples of structures include, but are not limited to, lesions within the human prostate that are less than 5 mm in size.

In the example depicted in FIG. 1, the ultrasonic transducer array 103 may be any one of a low, high, or ultra-high frequency ultrasonic transducer array. These ultrasonic transducer arrays may be used interchangeably with the signal processing pathway 100. For example, a low frequency ultrasonic transducer array (e.g., a curved linear abdominal transducer array having a transmit frequency centered around 3.5 MHz and having 128 ultrasonic transducer elements) may be used to provide a wide area scan of an abdomen. An operator might then replace the low frequency ultrasonic transducer with a medium frequency ultrasonic transducer (e.g., an endfire transrectal ultrasound transducer having a transmit frequency centered around 6.5 MHz and having 128 transducer elements) in order to obtain a more detailed scan of the prostate and bladder.

In another embodiment, the ultrasonic transducer array 103 may be capable of transmitting and receiving signals in the entirety of the frequency and voltage range of the signal processing pathway 100. That is, a singular ultrasonic transducer array 103 that can scan in the range of 1 MHz to 40 MHz can also be used.

A skilled person would understand that the voltage range required for transmitting a signal through an ultrasonic transducer array 103 is proportional to the frequency range of the ultrasonic transducer array 103. That is, driving a low frequency ultrasonic transducer array requires a higher voltage when compared to a higher frequency ultrasonic transducer array. For instance, an abdominal ultrasonic transducer centered in the 3.5 MHz frequency range may require that the signal have a voltage range of roughly −80V to +80V. An ultra-high frequency ultrasonic transducer array may require that the signal have a significantly lower voltage range. For example, an ultra-high resolution trans-rectal ultrasonic transducer centered in the 21 MHz frequency range may require that the signal have a voltage range of roughly −20V to +20V.

The signal processing pathway 100 is configured to handle this wide range of voltages. In some example embodiments, the components used in the signal pathway 100 are selected to be able to handle the frequency and voltage ranges required. In other embodiments, the signal pathway may also contain power monitoring subsystems to manage overcurrent situations.

For instance, in the example depicted in FIG. 1, the signal processing pathway is configured to handle a wide range of ultrasonic transducer arrays. These can include, but are not limited to, abdominal ultrasonic transducer arrays (centered at 3.5 MHz), endfire trans-rectal ultrasonic transducer arrays (centered at 6.5 MHz), and ultra-high resolution sidefire trans-rectal ultrasonic transducer arrays (centered at 21 MHz). In the example depicted in FIG. 1, the signal pathway 100 and its associated components are configured to handle the wide voltage range required to operate an ultrasonic transducer array 103 between 1 MHz and 40 MHz. In this example embodiment, the signal pathway 100 and its associated components are configured to handle a voltage range of at least −80V to +80V inclusive.

The signal processing pathway 100 is further configured to impedance match the various ultrasonic transducer arrays that could be used. It is known that elements in transducer arrays 103 operating at different center frequencies have different characteristic impedances. For example, a low frequency ultrasonic transducer array would have a relatively high impedance when compared to a higher frequency ultrasonic transducer array. The transmit pathway 106 and receive pathway 108 are configured to accommodate the different characteristic impedances of the ultrasonic transducer arrays 103 used in the system. A skilled person would understand that various impedance matching solutions may trade-off sensitivity, resolution, and/or bandwidth, or other factors related to the transmitted or received signal.

The signal processing pathway 100 is also communicatively connected to a data processing device. In an example embodiment, the data processing device may be any processing device designed for use in ultrasonic imaging devices 1000. The processing devices may be configured, for example, to generate human-usable images and video from the data collected from the ultrasonic transducer array 103 via the signal pathway 100. The data processing devices may also allow for raw, unprocessed data to be duplicated or shunted to another interface for further processing.

In another example the data processing device may be a general purpose computer (PC). Examples of a PC include, but are not limited to, general purpose computers having the following specifications: INTEL CORE i7 processor, 16 GB of random access memory, WiFi, 1 Gbps Ethernet, USB 3.0 ports, and a mass storage device such as a hard drive or solid state drive.

The signal processing pathway 100 may be configured on a peripheral device, expansion card, or daughterboard that can be connected to the PC. The connection may be any one of an external connection (e.g., USB 3.0, THUNDERBOLT, etc), an internal connection to the PC (e.g., via an expansion slot or bus), or an integrated circuit integrated directly on the motherboard of the ultrasonic imaging device.

Figure 2A:
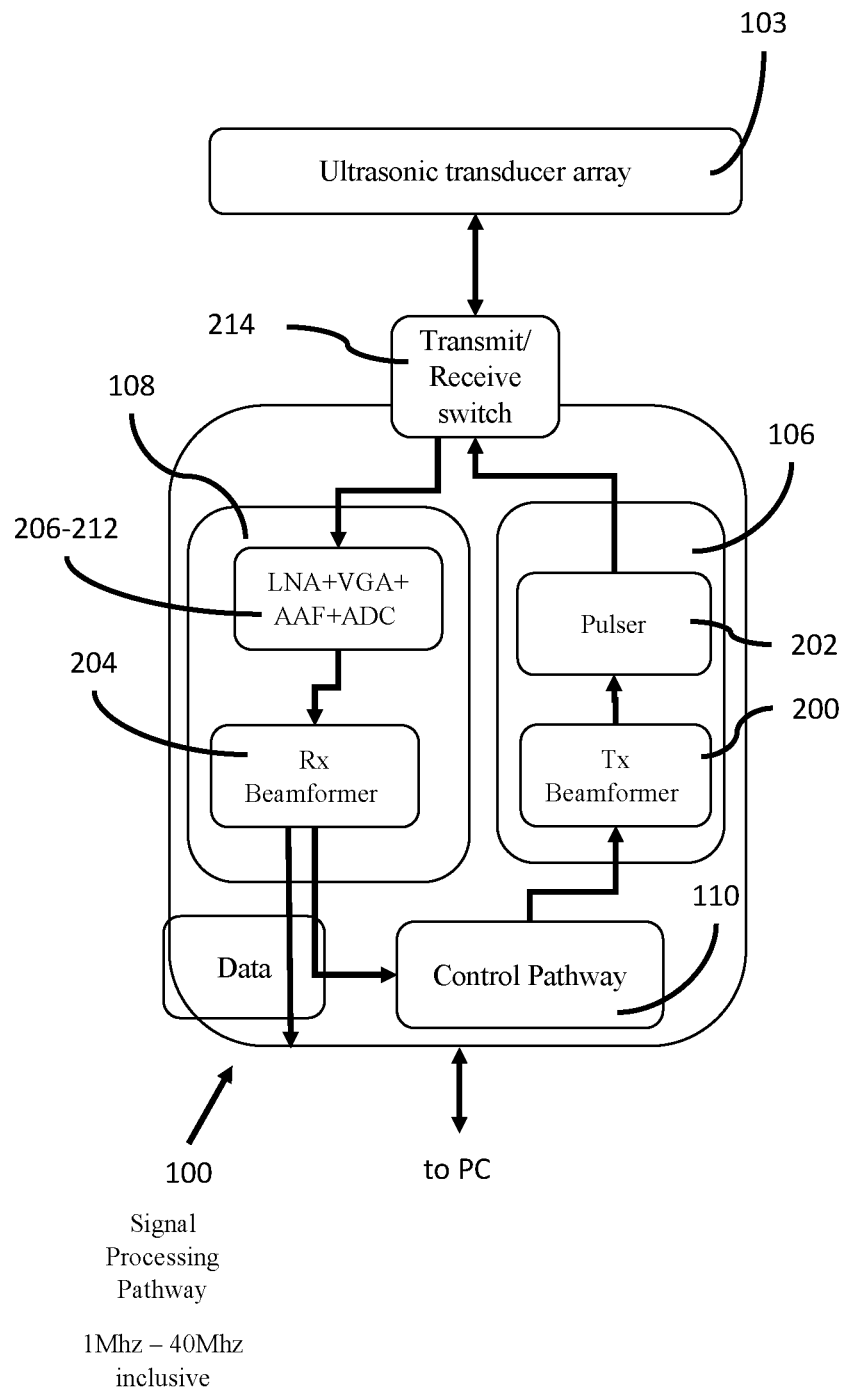
FIG. 2A (SHEET 2 of 28 SHEETS) is a block diagram showing an example configuration of FIG. 1.

Referring now to FIG. 2A, a block diagram showing an example embodiment of FIG. 1 is depicted. In this example configuration, the signal processing pathway has a transmit and receive switch 214. The transmit and receive switch 214 is provided for switching between the transmit pathway 106 and the receive pathway 108. In this example, the transmit and receive switch 214 is controlled by the control pathway. In the event where transmitting a signal from the ultrasonic transducer array 103 is desired, the transmit and receive switch 214 is commanded, via the control pathway 110, to activate the transmit pathway 106. Similarly, when receiving a signal from an ultrasonic transducer array 103 is desired, the transmit and receive switch 214 is commanded, via the control pathway 110, to activate the receive pathway 108.

Commercial examples of a transmit/receive switch 214 include, but are not limited to, a TEXAS INSTRUMENTS TX810 Programmable transmit/receive switch, and a MICROCHIP MD0105 High Voltage Protection Transmit/Receive Switch. A skilled person would understand that other suitable transmit/receive switches could be used without departing from the scope of this disclosure.

In the example provided in FIG. 2A, the transmit pathway 106 includes a pulser 202 and a transmit beamformer 200.

The transmit beamformer 200 is configured to, among other things, generate, at least in part, the transmit signals that will be applied to the ultrasonic transducer elements in the ultrasonic transducer array 103.

It is known that a transmit signal can be directed towards a desired location by adjusting, via a transmit beamformer, the transmit signal to the ultrasonic transducer array 103. That is, properties of the transmit signal such as, but not limited to, the scanning depth, f-number, and steering angle can be adjusted using the transmit beamformer. The transmit beamformer 200 adjusts the waveform so that the transmit signal can be focused to a specified direction and depth from the transducer array. By way of a non-limiting example, the transmit signals can be uniquely delayed and/or apodized to direct the ultrasonic wavefront to a small area at 15 mm depth.

The pulser 202 is configured to adjust the voltage range of the waveform so that the voltage of the transmit signal can appropriately drive the ultrasonic transducer in the ultrasonic transducer array 103. For example, the pulser 202 may increase the voltage range of a beamformed transmit signal to +/−80V so that the beamformed signal can be used with an abdominal ultrasonic transducer array. A skilled person would also understand that a pulser 202 is provided for each channel in the transmit pathway 106.

Once the beamformed transmit signal has been transmitted from the ultrasonic transducer array 103, a control signal, via the control pathway 110, instructs the transmit and receive switch 214 to switch to the receive pathway 108. Signal from the tissue being imaged are reflected back to the ultrasonic transducer array 103 based on the speed of sound in the tissue. The reflected signal is received by the ultrasonic transducer array 103 and then sent to the receive pathway 108 for processing.

In the example provided in FIG. 2A, the receive pathway includes a Low Noise Amplifier (LNA) 212, Variable Gain Amplifier (VGA) 208, Anti-Aliasing Filter (AAF) 210, and an Analog to Digital Converter (ADC) 206. A skilled person would understand that these devices are configured to convert, clean, and amplify the signal received from the ultrasonic transducer array for further processing. A skilled person would also understand that these devices would be provided for each channel in the receive pathway 108.

Figure 2B:
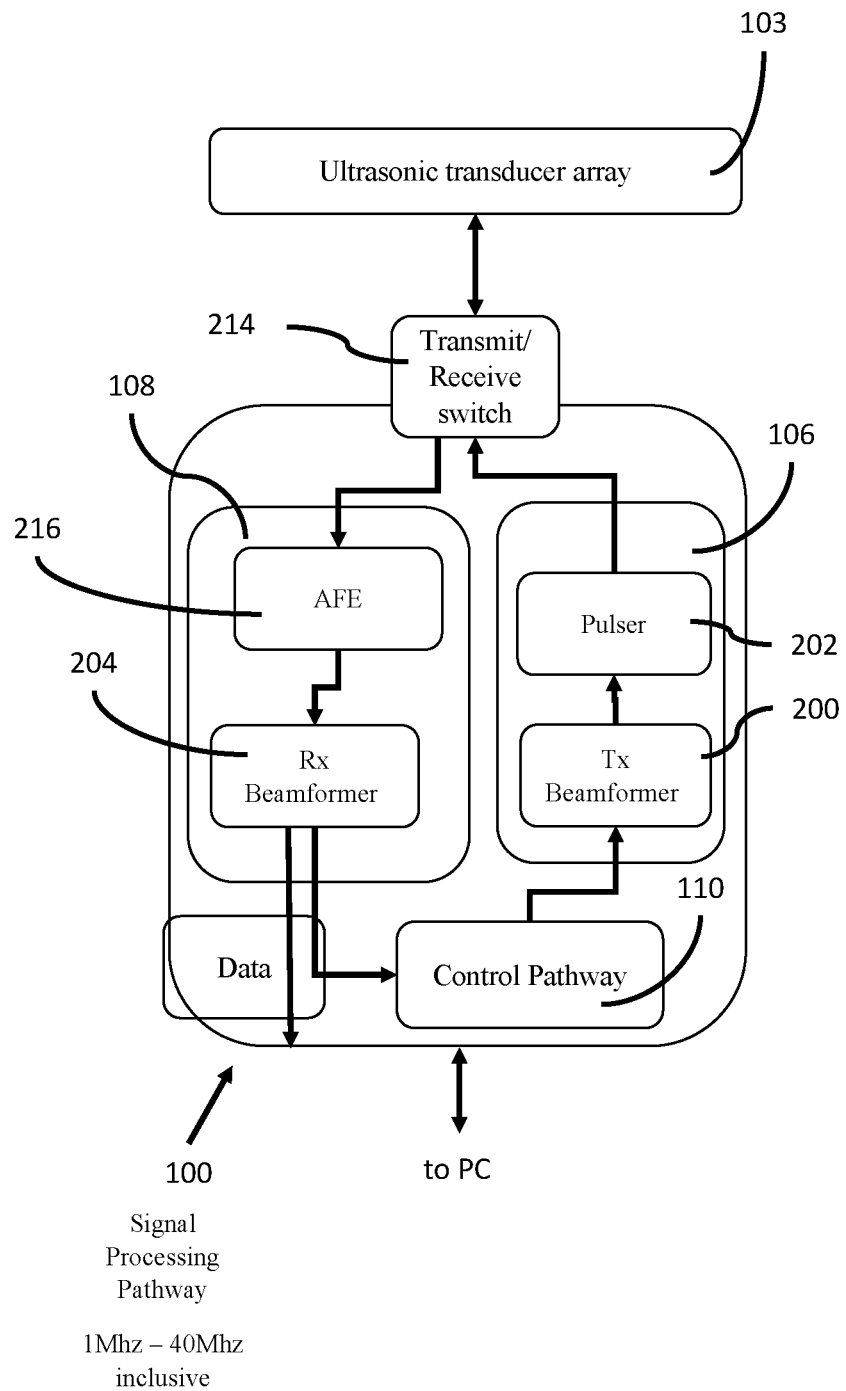
FIG. 2B (SHEET 3 of 28 SHEETS) is a block diagram showing an example configuration of FIG. 1.

Referring now to FIG. 2B, in the example depicted the LNA 212, VGA 208, AAF 210, and ADC 206 may be integrated into an Analog Front End (AFE). This AFE may be an integrated circuit having the functionality of the LNA 212, VGA 208, AAF 210, and ADC 206.

In the example provided in FIG. 2A, the receive pathway 108 further includes a receive beamformer 204. The receive beamformer 204 is configured, at least in part, to process the received signals (or beamform). This can include, but is not limited to, any combination of uniquely delaying, apodizing, and summing the received signals.

In another embodiment, the receive beamformer does not sum the received signals so that the beamforming can be completed on a PC, GPU, and/or data processor. Also, the receive beamformer optionally does not delay and/or apodize the received signals.

Once the received signals have been processed by the receive beamformer 204, the signal is sent, via a data bus, to the data processing device for additional processing.

It will be understood that, generally, each ultrasonic transducer element in the ultrasonic transducer array 103 has an associated channel in the signal processing pathway 100. That is, the signal processing pathway 100 generally has as many channels as there are ultrasonic transducer elements in an ultrasonic transducer array 103. For example, in order to operate with an ultrasonic transducer array having 64 ultrasonic transducer elements, the signal processing pathway 100 should have 64 channels.

It is further understood that the scanning field of view (FOV) of an ultrasonic scanning device is proportional, at least in part, to the number of elements in an ultrasonic transducer array 103. Thus, the signal processing pathway 100 should have a sufficient number of channels to maintain a usable field of view for the object being scanned. For instance, in the case of a human prostate it was found that a signal processing pathway 100 having 128 channels was sufficient for a curved linear end-fire 6.5 MHz transducer to scan and maintain a usable field of view for trans-rectal ultrasonic transducer arrays 103. A skilled person would understand that transducers operating at different center frequencies may require fewer or additional channels. For instance, a 21 MHz side-fire transducer may require additional channels in order to maintain a usable field of view. In the non-limiting example where the usable field of view is for trans-rectal prostate exams, the signal processing pathway may require, for example, 512 channels.

Generally, the resolution of an ultrasonic transducer array 103 is related to the scanning frequency of the ultrasonic transducer array 103. That is, the higher the scanning frequency, the higher the resolution. A tradeoff, however, is that the FOV for the ultrasonic transducer array 103 decreases as the scanning frequency increases. One possible way to increase the field of view for a higher frequency ultrasonic transducer array 103 is to increase the number of ultrasonic transducer elements that are transmitting.

One method of increasing the number of ultrasonic transducer elements being driven in an ultrasonic transducer array 103 is to increase the number of channels in the signal processing pathway 100. This is because, generally, a channel is assigned to a corresponding ultrasonic transducer element in the ultrasonic transducer element array 103.

Due to cost, space, power, or other limitations, however, it may not be possible to provide a sufficient number of channels in a signal processing pathway 100 to achieve the desired resolution. In these circumstances, other ways of increasing the number of ultrasonic transducer elements being driven per signal processing pathway channel, in order to increase the FOV, can be contemplated. For instance, in an example embodiment a transducer element multiplexer 300 can be used to drive more ultrasonic transducer elements than there are channels in the signal processing pathway 100.

Figure 3:
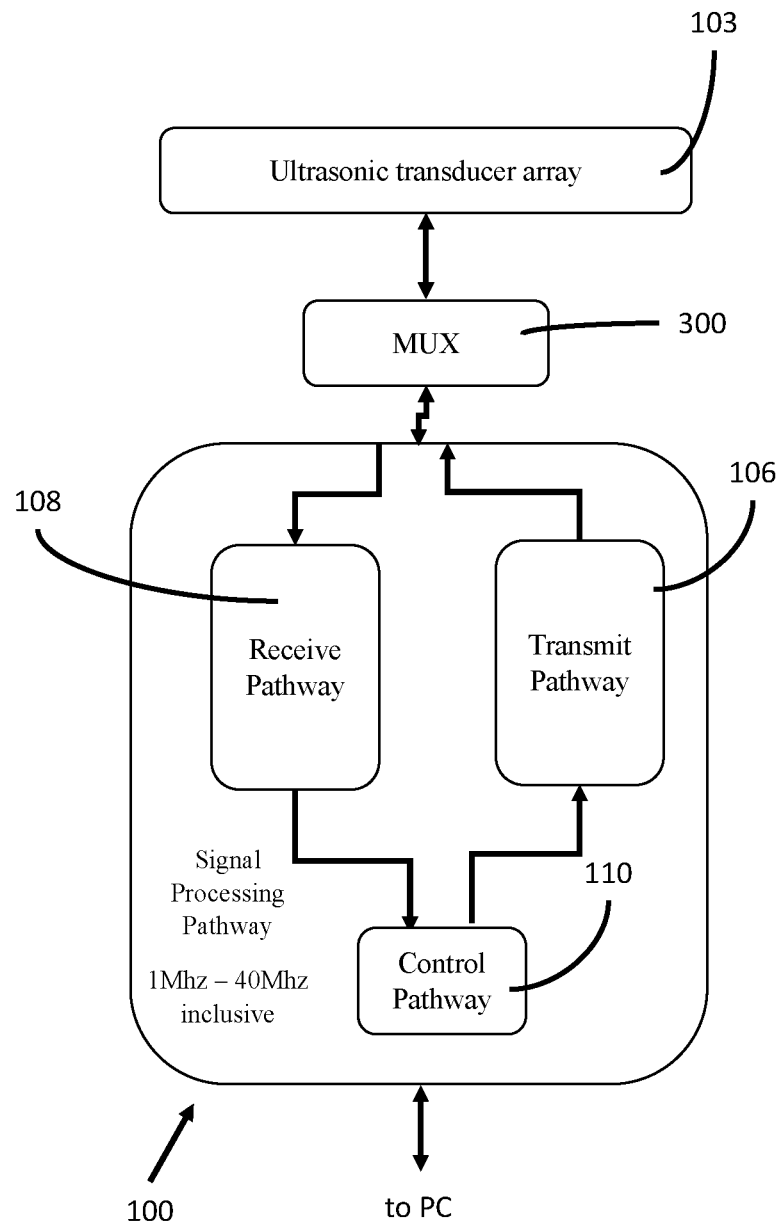
FIG. 3 (SHEET 4 of 28 SHEETS) is a block diagram of an example configuration of FIG. 1, the signal pathway having a multiplexer for simultaneously driving more than one ultrasonic transducer element in the ultrasonic transducer array.
Figure 4:
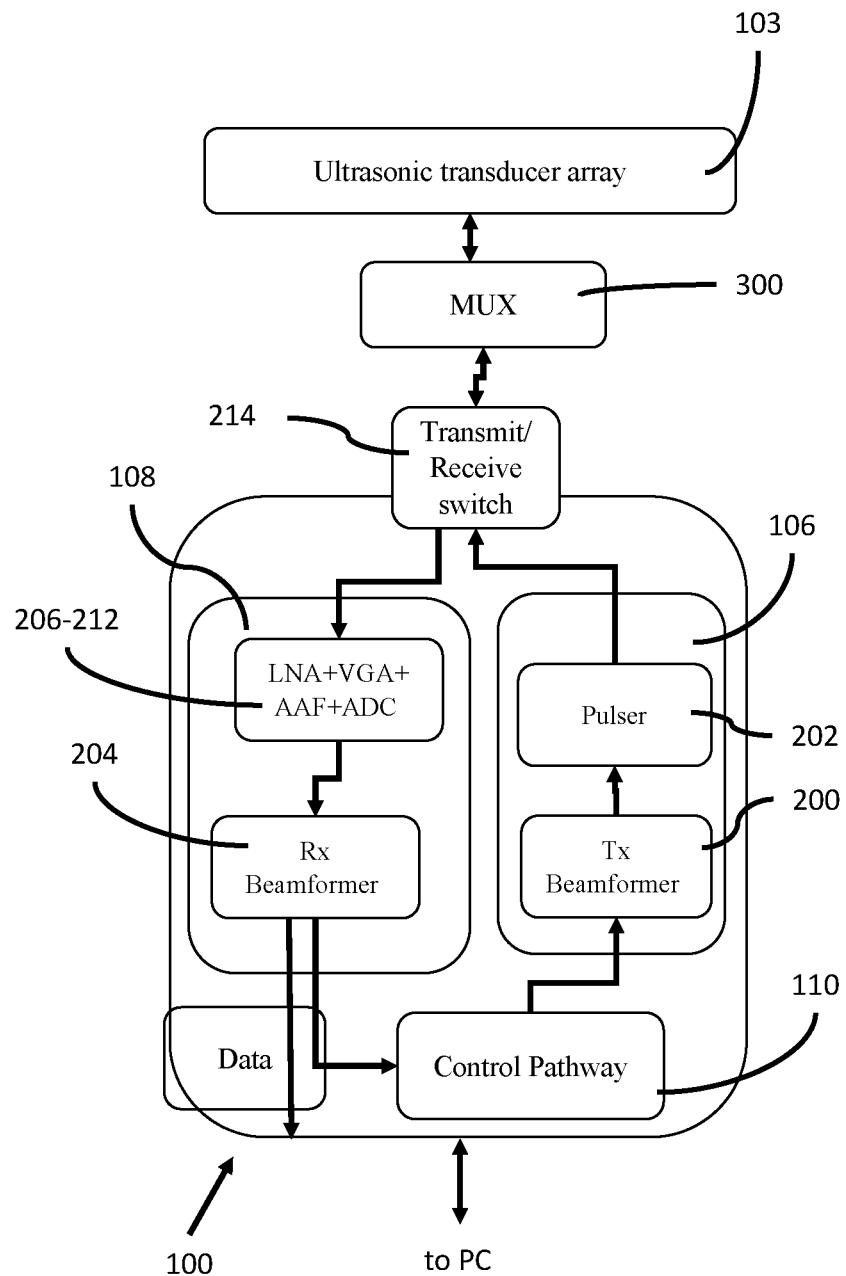
FIG. 4 (SHEET 5 of 28 SHEETS) is a block diagram of an example configuration of FIG. 2A, the signal pathway having a multiplexer for simultaneously driving more than one ultrasonic transducer element in the ultrasonic transducer array.
Figure 5:
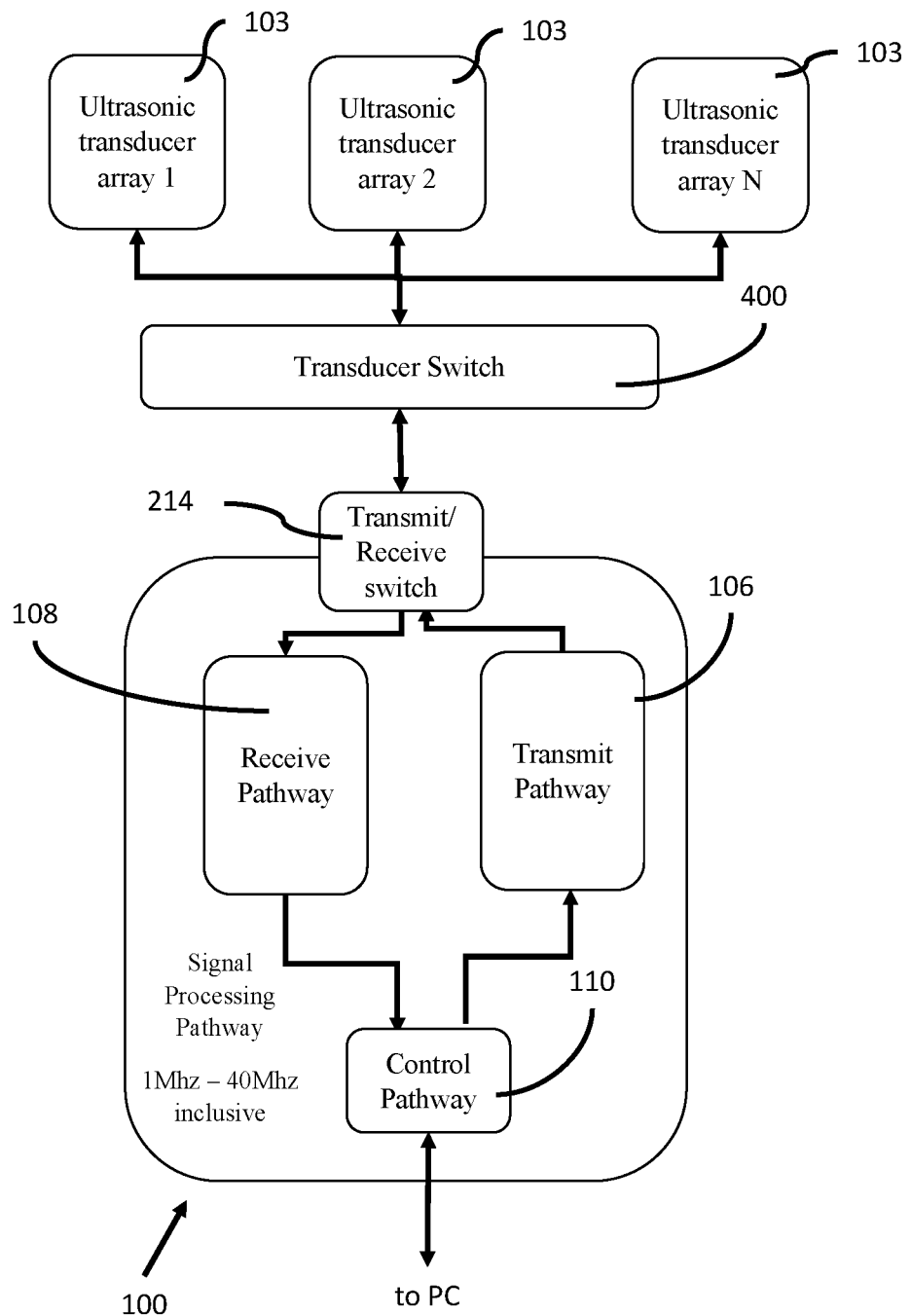
FIG. 5 (SHEET 6 of 28 SHEETS) is a block diagram of an example configuration of FIG. 1, the signal pathway configured to operate with N ultrasonic transducer arrays.
Figure 6:
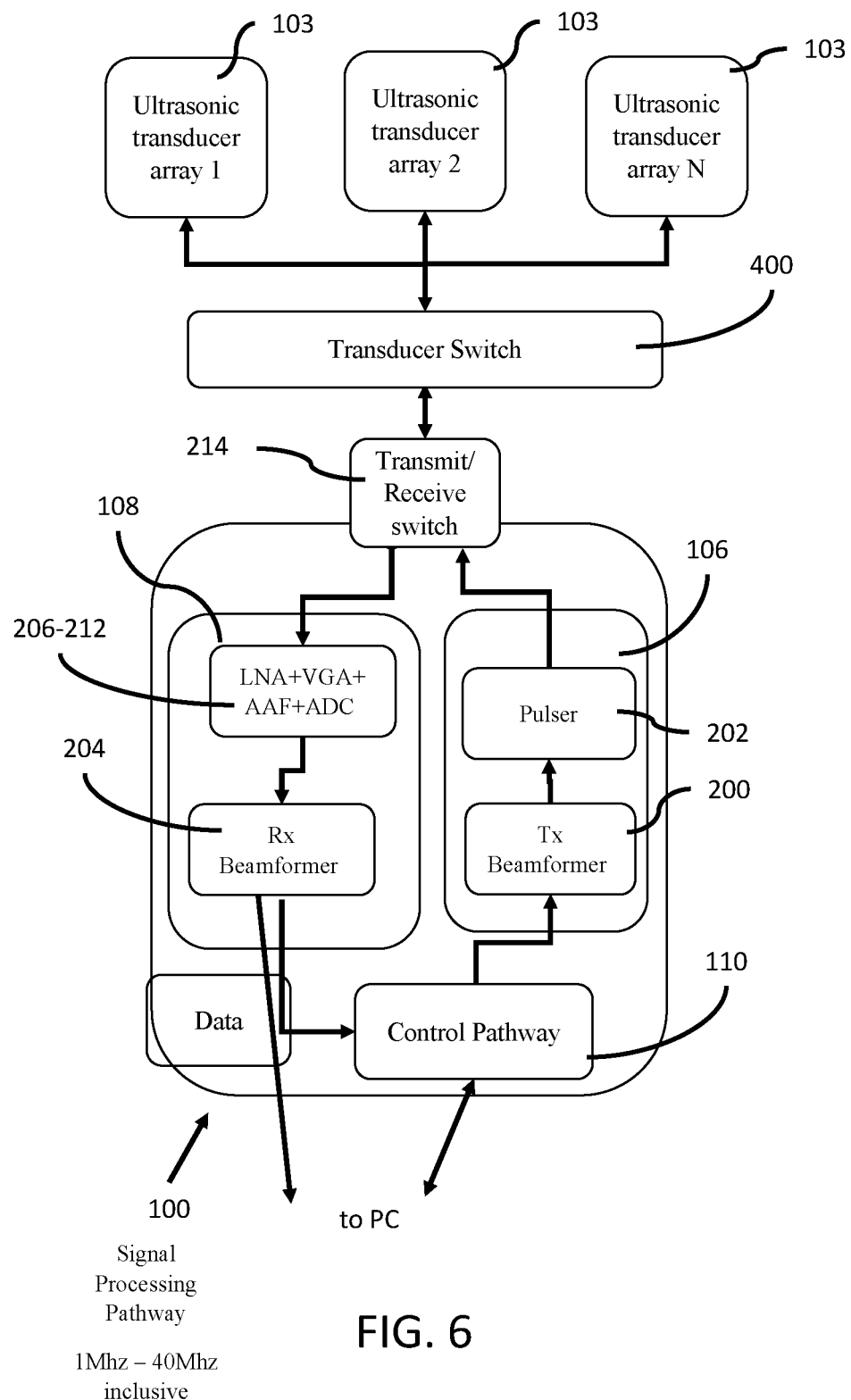
FIG. 6 (SHEET 7 of 28 SHEETS) is a block diagram of an example configuration of FIG. 2A, the signal pathway configured to operate with N ultrasonic transducer arrays.
Figure 7:
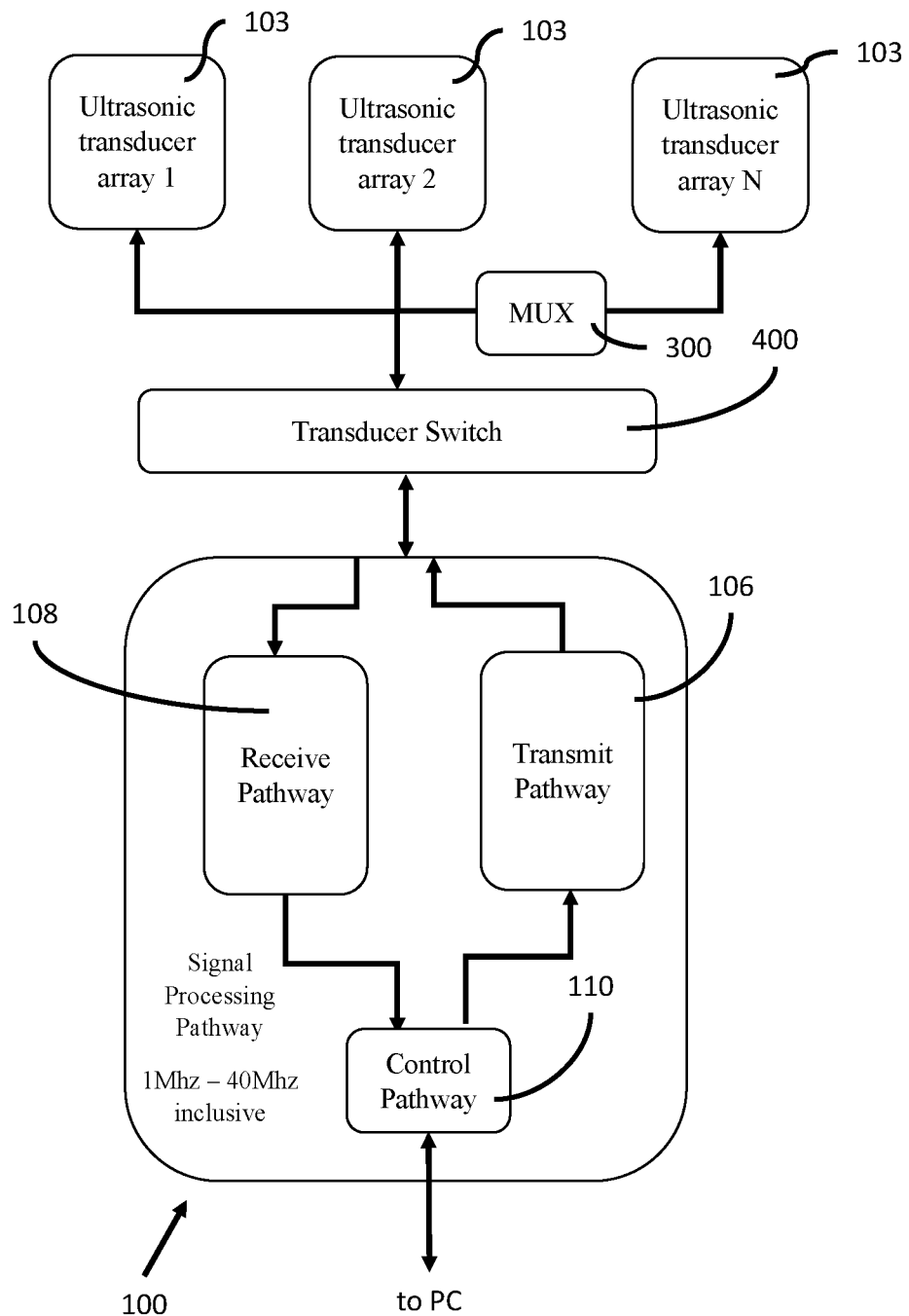
FIG. 7 (SHEET 8 of 28 SHEETS) is a block diagram of an example configuration of FIG. 1, the signal pathway configured to operate with N ultrasonic transducer arrays and the signal pathway having a multiplexer for simultaneously driving more than one ultrasonic transducer element in the ultrasonic transducer array.
Figure 8:
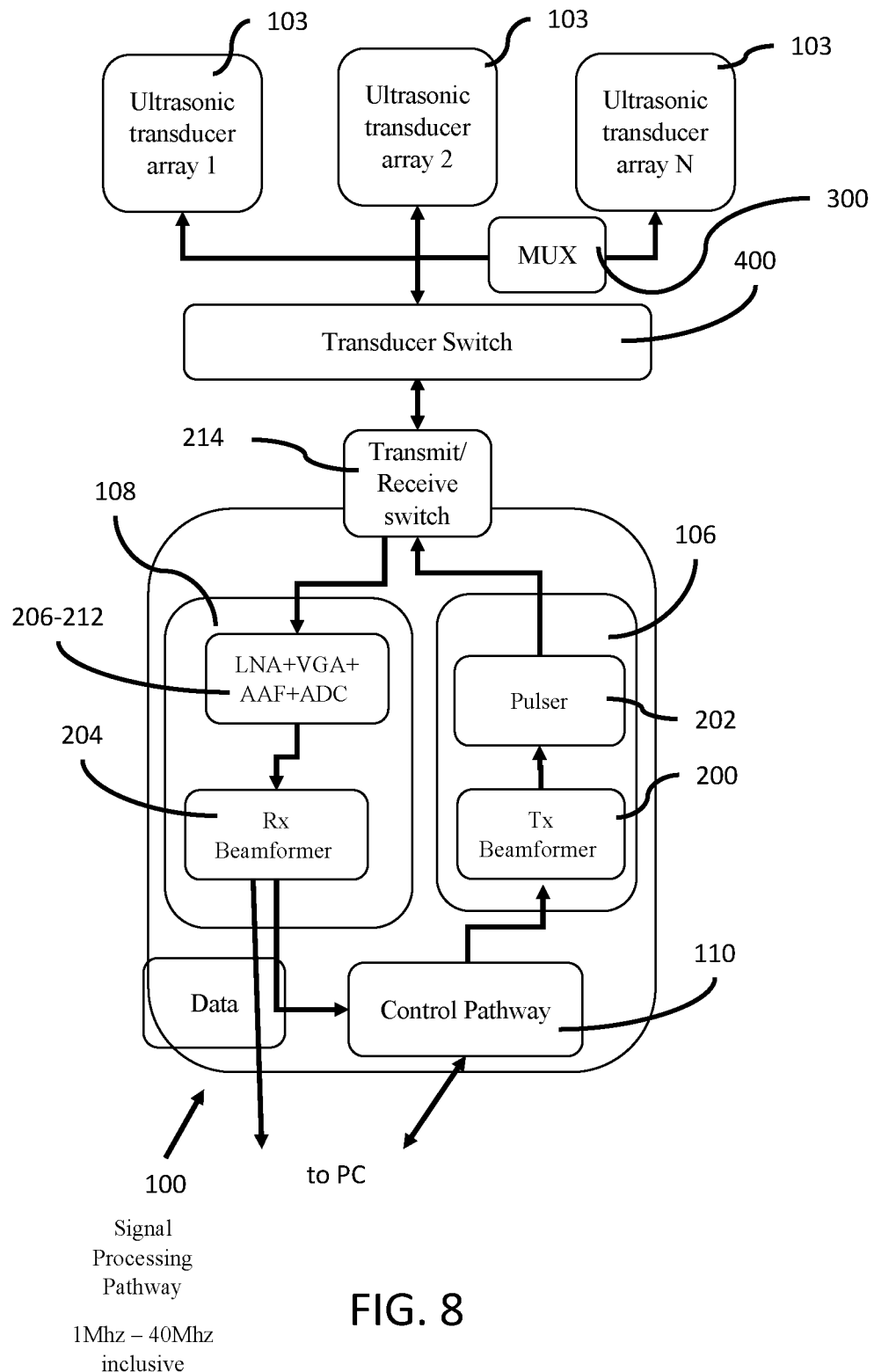
FIG. 8 (SHEET 9 of 28 SHEETS) is a block diagram of an example configuration of FIG. 2A, the signal pathway configured to operate with N ultrasonic transducer arrays and the signal pathway having a multiplexer for simultaneously driving more than one ultrasonic transducer element in the ultrasonic transducer array.
Figure 9:
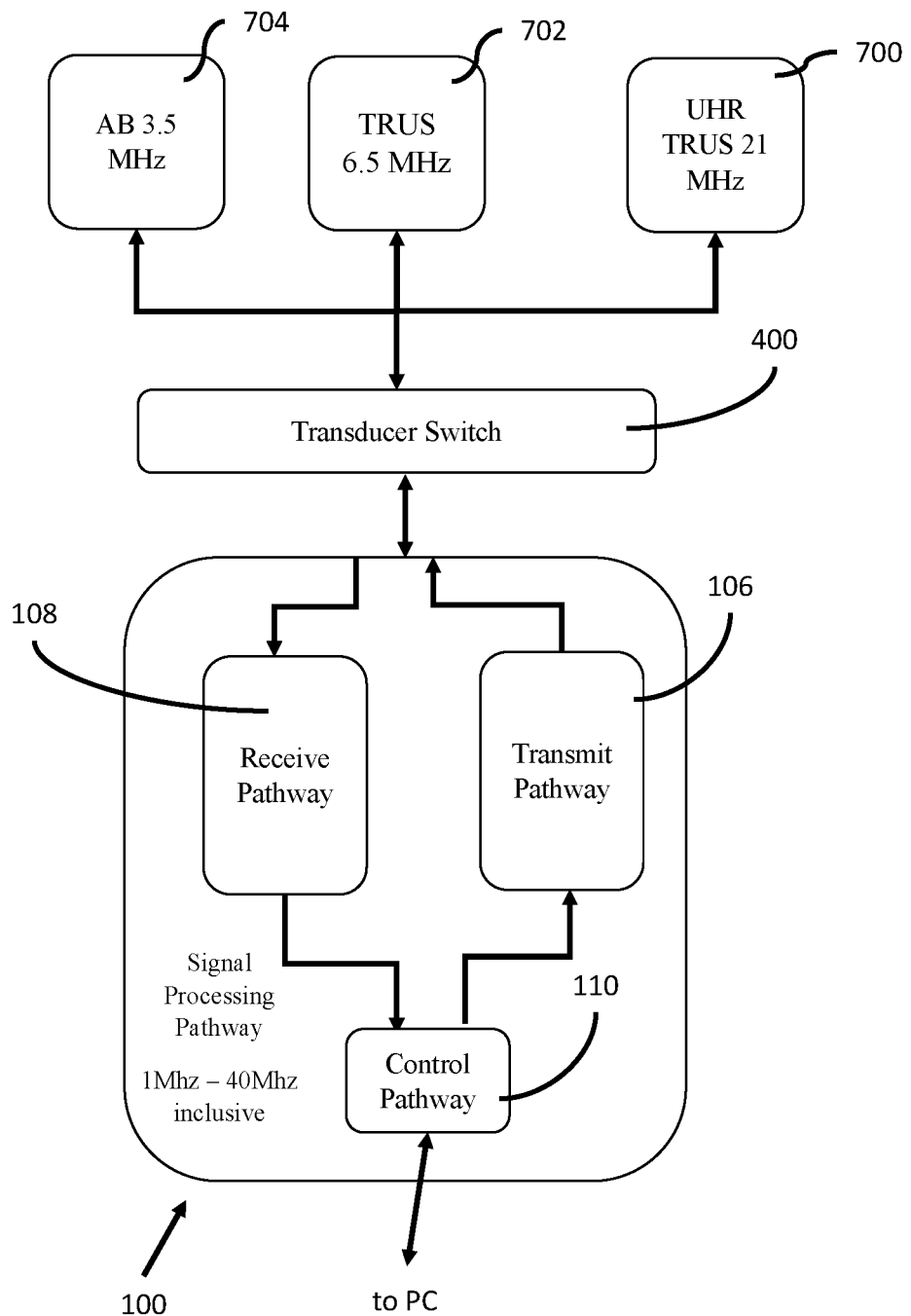
FIG. 9 (SHEET 10 of 28 SHEETS) is a block diagram of an example configuration of FIG. 1, the signal pathway configured to operate with an abdominal (3.5 MHz), a trans-rectal (6.5 MHz), and an ultra-high resolution trans-rectal (21 MHz) ultrasonic transducer arrays.
Figure 10:
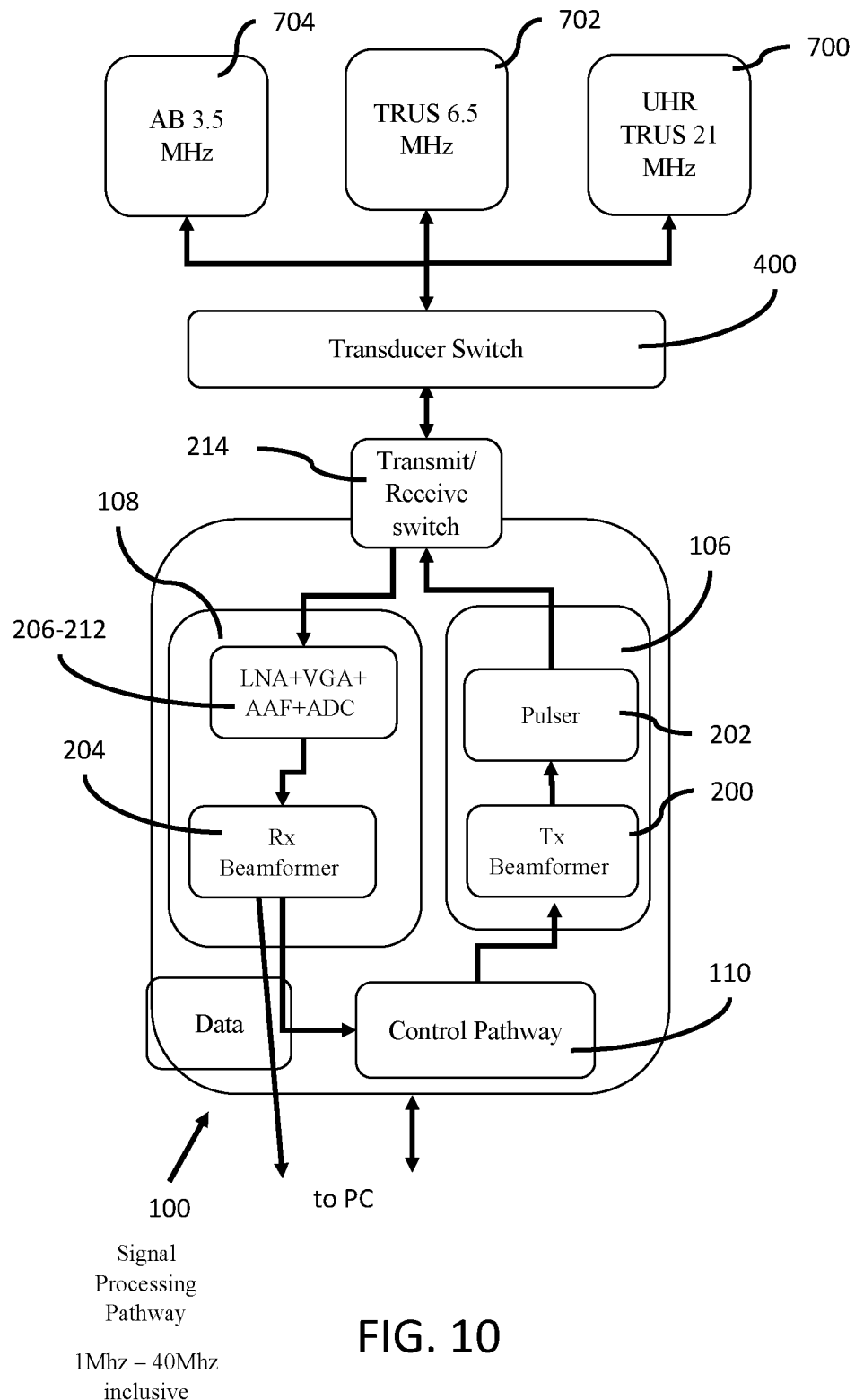
FIG. 10 (SHEET 11 of 28 SHEETS) is a block diagram of an example configuration of FIG. 2A, the signal pathway configured to operate with an abdominal (3.5 MHz), a trans-rectal (6.5 MHz), and an ultra-high resolution trans-rectal (21 MHz) ultrasonic transducer arrays.
Figure 11:
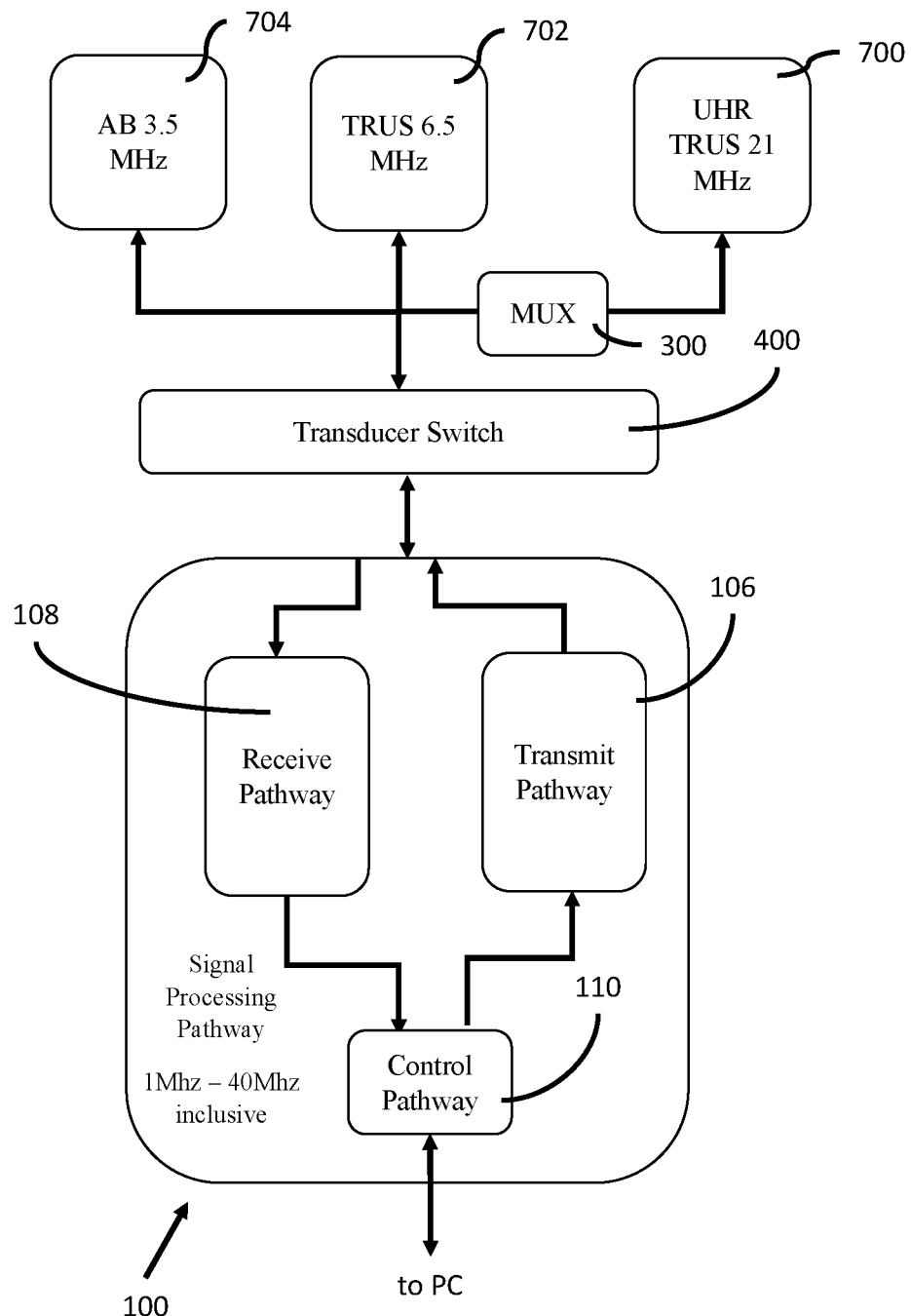
FIG. 11 (SHEET 12 of 28 SHEETS) is a block diagram of an example configuration of FIG. 1, the signal pathway configured to operate with an abdominal (3.5 MHz), a trans-rectal (6.5 MHz), and an ultra-high resolution trans-rectal (21 MHz) ultrasonic transducer arrays, and the signal pathway having a multiplexer for simultaneously driving more than one ultrasonic transducer element in the ultrasonic transducer array.
Figure 12:
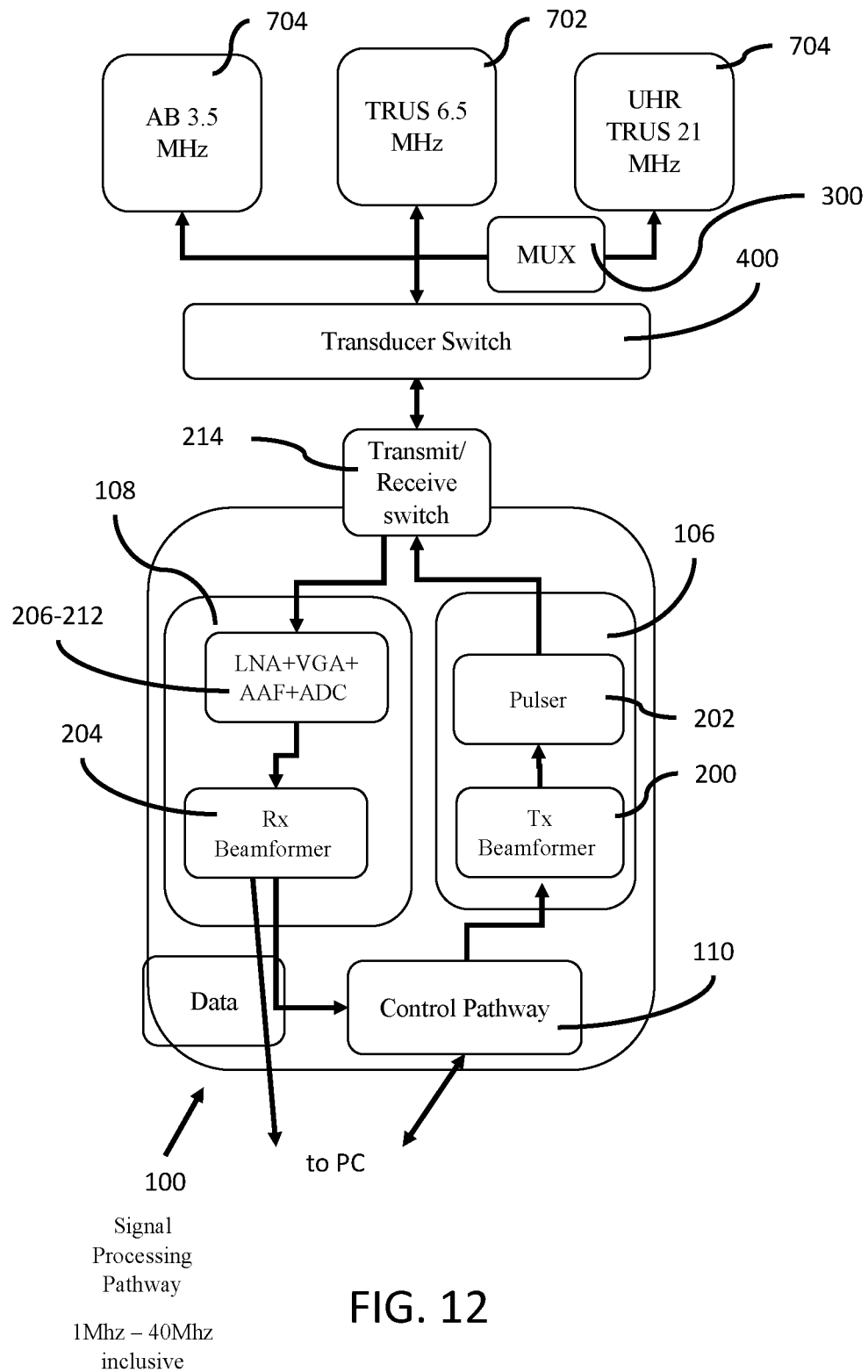
FIG. 12 (SHEET 13 of 28 SHEETS) is a block diagram of an example configuration of FIG. 2A, the signal pathway configured to operate with an abdominal (3.5 MHz), a trans-rectal (6.5 MHz), and an ultra-high resolution trans-rectal (21 MHz) ultrasonic transducer arrays, and the signal pathway having a multiplexer for simultaneously driving more than one ultrasonic transducer element in the ultra-high resolution ultrasonic transducer array.

Referring now to FIG. 3 and FIG. 4, which are embodiments of FIG. 1 and FIG. 2A respectively, a transducer element multiplexer 300 is provided on the signal path 100 in order to mitigate, at least in part, the problem of driving more ultrasonic transducer elements than there are channels in the signal processing pathway 100.

The transducer element multiplexer 300 allows more than one ultrasonic transducer element in the ultrasonic transducer element array 103 to be driven for each channel in the signal pathway 100. This allows an increase in the FOV for the ultrasonic transducer array 103 while maintaining the desired resolution without having to increase the number of channels in the signal pathway 100.

The multiplexer 300 switches which elements are active between each ultrasound line within the ultrasound image so that lines can be acquired using the elements from different spatial locations along the array. For example, for a line on the left edge of the imaging field of view, the elements closest to that edge may be selected, while for a line on the right edge of the imaging field of view the elements closest to that edge may be selected. Using elements close to the line being acquired is useful to avoid artifacts and signal loss due to beam steering, and permits a larger FOV to be captured. This is equivalent to stacking N ultrasonic transducer element arrays beside each other and generating an image on each separately and then combining those images.

Simultaneously in the context of simultaneously driving more than one ultrasound transducer element refers to the ability to switch between individual ultrasound transducer elements or groups of ultrasound transducer elements within one ultrasound image acquisition period without materially affecting the frame rate of acquisition.

In the examples depicted in FIG. 3 and FIG. 4, the transducer element multiplexer 300 selects, at least in part, the transmit signal being sent through the channels in the signal processing pathway 100. These replicated signals are then sent to the ultrasonic transducer elements in the ultrasonic transducer element array 103. That is, a signal being sent through a single channel of the signal processing pathway 100 may be used to activate more than one ultrasonic transducer element in the ultrasonic transducer array 103.

Once the reflected signal is received, the transducer element multiplexer 300 may also select, at least in part, the reflected signal from one of a set of individual transducer elements so that the selected reflected signal can be sent to a single channel in the signal processing pathway 100.

For instance, in some examples a 4:1 transducer element multiplexer 300 may be used to maintain a usable field of view for an ultra-high resolution trans-rectal ultrasound transducer array. In the case where the signal pathway 100 has 128 channels, the 4:1 transducer element multiplexer 300 would be able to drive 512 (128×4) ultrasonic transducer elements in the ultra-high resolution trans-rectal ultrasound transducer array. Similarly, when the 512 ultrasonic transducer elements in the ultra-high resolution trans-rectal ultrasound transducer array receive the reflected signal, the 4:1 transducer element multiplexer 300 is configured to select, in groups of 128 elements, the received data from the 512 individual transducer elements to 128 signals (512/4) for transmission through the 128 channels of the signal processing pathway 100.

In another example, the transducer element multiplexer 300 may allow for a selectable multiplexer. For example, the transducer element multiplexer 300 may selectably allow for driving 4, 3, or 2 ultrasonic transducer elements for each channel in the signal processing pathway 100 (e.g., a selectable 4:1, 3:1, and 2:1 transducer element multiplexer). This would allow for a multiple fields of view for the ultrasonic transducer array 103.

Referring now to FIG. 5, FIG. 6, FIG. 7, and FIG. 8, in some embodiments the signal processing pathway 100 is operable with more than one ultrasonic transducer array 103. In these embodiments, a transducer switch 400 is provided. The transducer switch 400 is configured to selectably switch between the multiple ultrasonic transducer arrays 103.

In some examples, the ultrasonic imaging device 1000, via the control pathway 110, may automatically select the appropriate ultrasonic transducer array 103 based on the dimensions of the object to be scanned. For instance, if a user selects the scanning parameters for targeted prostate structures for biopsy, the ultrasonic imaging device 1000 will issue a command, via the control pathway 110, to the transducer switch 400 to switch to an ultra-high resolution ultrasonic transducer array 103 that is appropriate for scanning targeted prostate structures for biopsy. Examples of targeted prostate structures for biopsy include, but are not limited to, lesions in the prostate that are smaller than 5 mm.

Alternately, the transducer switch 400 may be a manual switch whereby a user can manually select which ultrasonic transducer array 103 to use.

In yet another example, the transducer switch 400 may be a part of a hot-swap mechanism that allows users to plug and unplug ultrasonic transducer arrays 103 as required. This allows for different ultrasonic transducer arrays 103 to be used in the same signal processing pathway 100. In the embodiments depicted in FIG. 5 to FIG. 12, for instance, the attached ultrasonic transducer arrays 103, 700, 702, 704, may be recognized using a transducer ID. Once an ultrasonic transducer array having a transducer ID is inserted into the hot-swap system, the transducer switch 400 can then initialize the ultrasonic transducer array 103 for use in the ultrasonic imaging system 1000.

In another example embodiment, the transducer switch 400 may have connectors for each of the ultrasonic transducer arrays 103. The transducer switch 400 may also include one or more latching relays to allow the system to switch between one or more ultrasonic transducer arrays 103. Control of the latching relays (and other solid-state switches for digital signals) will be through the control path.

It should be clear that the ultrasonic transducer arrays 103 (each having a respective voltage and frequency range) should operate within the frequency and voltage range of the signal processing pathway 100. In some embodiments, the ultrasound imaging device 1000 will raise a warning when an ultrasonic transducer array 103 that is incompatible with the signal processing pathway 100 is attached. This warning can include, but is not limited to, alerting a user of the incorrectly inserted ultrasonic transducer array.

Referring now to FIG. 9, FIG. 10, FIG. 11, and FIG. 12, these figures depict various signal pathways 100 having combinations of the features described herein.

Typically, individual ultrasonic transducer arrays 103 are limited in their frequency scanning range. For example, ultrasonic transducer arrays 103 configured for scanning a large portion of a human abdominal cavity (i.e., abdominal ultrasonic transducer arrays) generally operate in the 3.5 MHz range. Scanning smaller objects such as a specific organ or part of an organ requires higher frequency ultrasonic transducer arrays. For instance, scanning a human prostate typically requires a trans-rectal ultrasonic transducer which typically operates in the 6.5 MHz range. For seeing structural detail within the human prostate (for example, urethra, ejaculatory duct, lesions smaller than 5 mm) an ultra-high frequency trans-rectal ultrasonic transducer that operates in the 21 MHz range may be required.

The signal pathway 100 is configured to be operable with an ultrasonic transducer array 103 that has a transmit frequency in the range of 1 MHz to 40 MHz and a voltage range of +/−80V. This frequency range includes the frequency ranges of any combination of an abdominal ultrasonic transducer array, trans-rectal ultrasonic transducer array, and ultra-high frequency trans-rectal ultrasonic transducer array.

Figure 13:
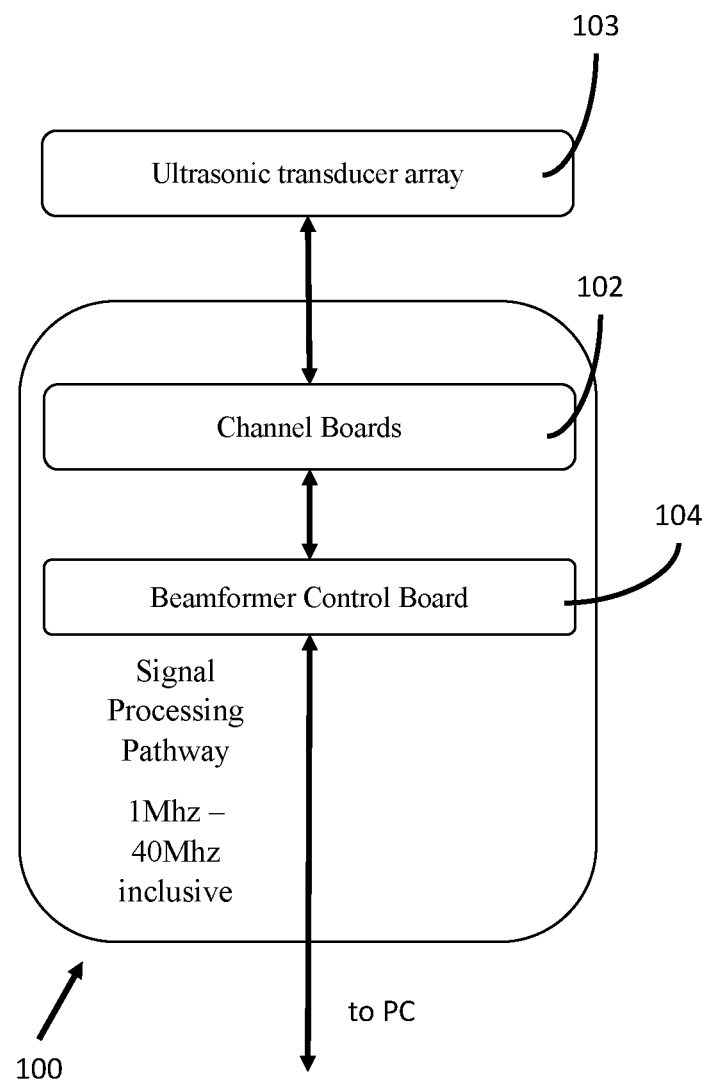
FIG. 13 (SHEET 14 of 28 SHEETS) is a block diagram of an embodiment where the signal path 100 is configured on a channel board and a beamformer control board.
Figure 14:
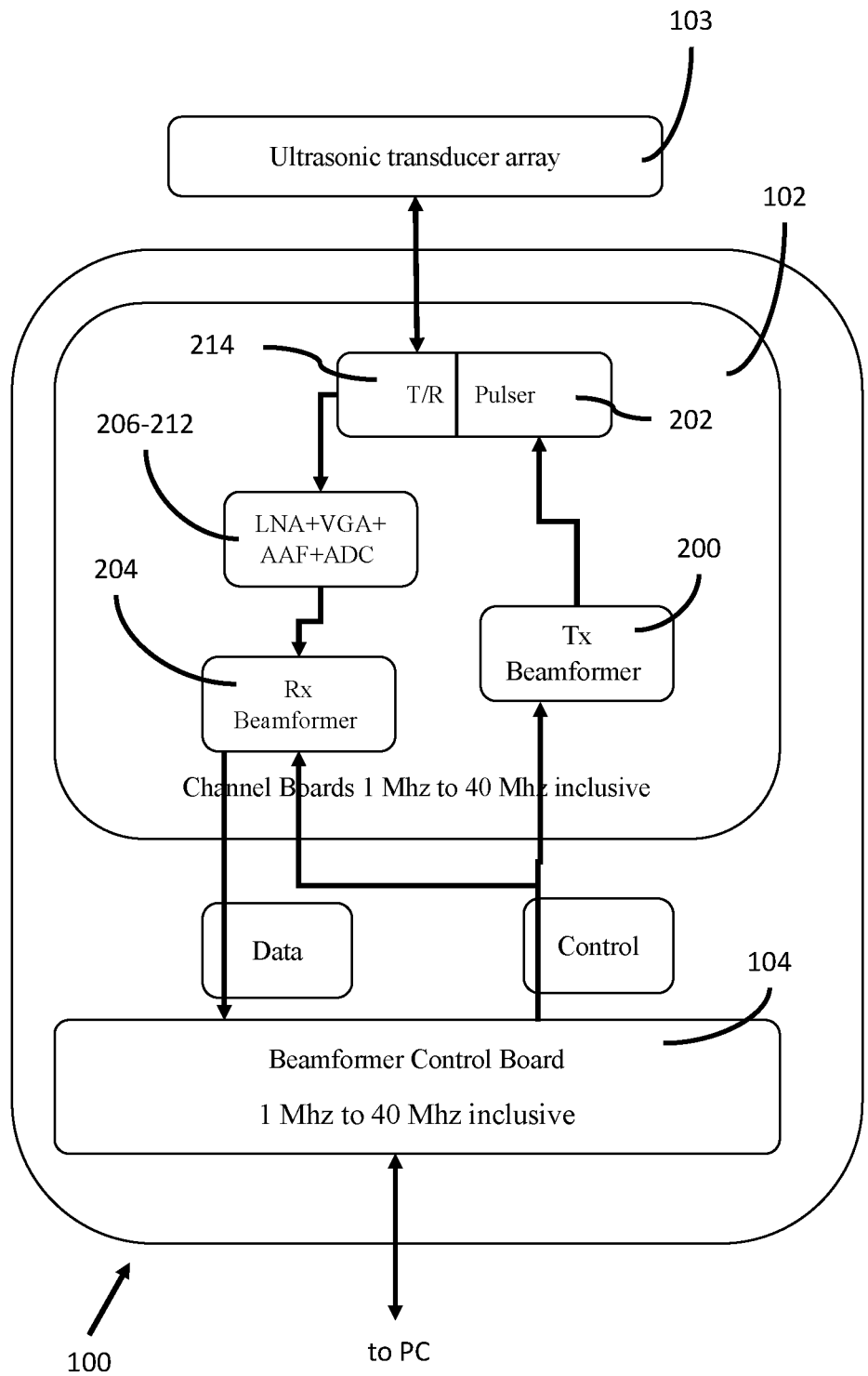
FIG. 14 (SHEET 15 of 28 SHEETS) is a block diagram showing an example configuration of FIG. 13.

Referring now to FIG. 13 and FIG. 14, alternate embodiments of FIG. 1 and FIG. 2A are depicted. In these examples the signal processing pathway 100 comprises a channel board 102 and a beamformer control board 104. That is, both the transmit pathway 106 and the receive pathway 108, and the control pathway 110 of FIG. 1 and FIG. 2A are implemented, at least in part, on the channel board 102 and the beamformer control board 104.

The channel board 102 is configured to generate the transmit signals to the ultrasonic transducer array 103. These signals are then used by the ultrasonic transducer array 103 to ultrasonically scan a body. By way of example, the signals transmitted to the ultrasonic transducer array 103 are converted from an electrical signal to an analog, ultrasonic signal, and the ultrasonic signal is transmitted to the body.

The channel board 102 is also configured to receive data scanned from the ultrasonic transducer array 103. By way of example, the ultrasonic transducer array 103 receives, or acquires, reflected ultrasonic signals. These ultrasonic signals are then converted to an electrical signal that is then sent to the control board. The control board then processes, at least in part, the received signal. The processed received signal is then sent to the beamformer control board 104 for further processing.

The ultrasonic imaging device 1000 can have more than one channel board 102. Spatial, heat, bandwidth, or other considerations may require that more than one channel board 102 be provided for the ultrasonic imaging device 1000. In one example embodiment, a signal pathway 100 having 128 channels is made up of two identical channel boards 102, each channel board having 64 channels. In another configuration, a single channel board 102 may contain all 128 channels.

In the embodiment depicted in FIG. 13 and FIG. 14, the beamformer control board 104 is configured to, at least in part, to process both the signal transmitted to, and the signal received from, the ultrasonic transducer array 103.

In some embodiments, the beamformer control board provides the main data uplink to the PC or data processor. The beamformer control board 104 may also process, at least in part, the received signal before sending it to the PC or data processor. For example, the beamformer control board 104 may partially sum the received signal data before sending it to the PC or data processor.

In some embodiments the control pathway 110 may be implemented, at least in part, in any combination of the channel board 102 and the beamformer control board 104. In the examples provided in FIG. 13 and FIG. 14, commands from the data processor may be passed through the beamformer control board 104 and the channel board 102. These commands can include, but are not limited to, selecting the appropriate ultrasonic transducer array 103, directing the beamformer control board 104 to apply a specific beamformed pattern to a transmitted or received signal, or activating a transducer multiplexer 300 to change the FOV for the ultrasonic transducer array 103.

Figure 15:
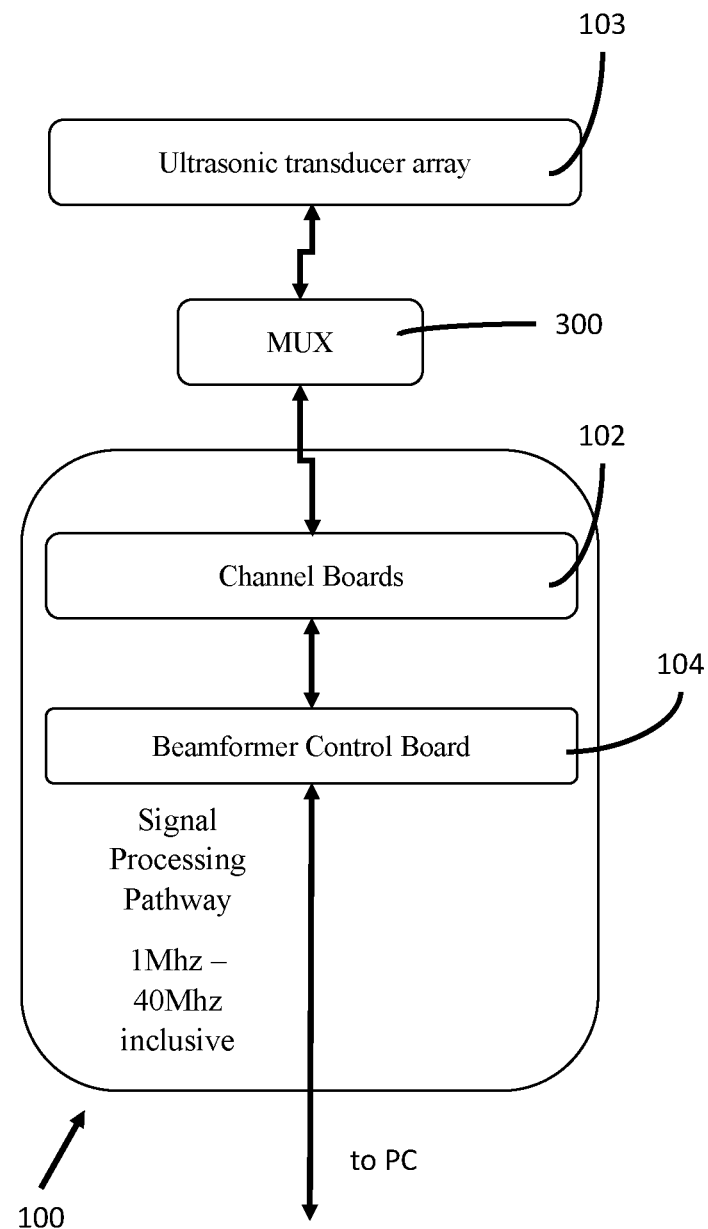
FIG. 15 (SHEET 16 of 28 SHEETS) is a block diagram of an example configuration of FIG. 13, the signal pathway having a multiplexer for simultaneously driving more than one ultrasonic transducer element in the ultrasonic transducer array.
Figure 16:
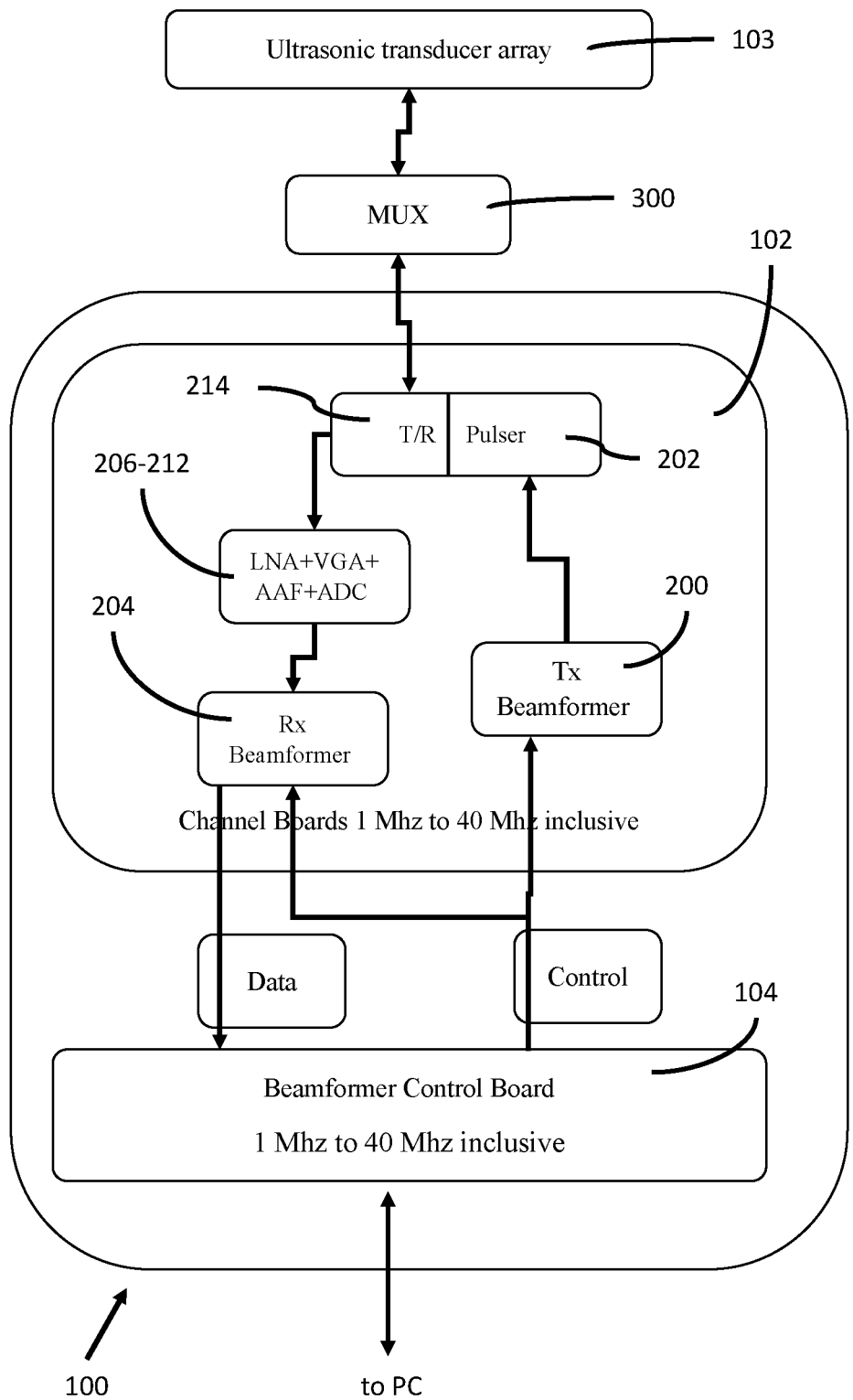
FIG. 16 (SHEET 17 of 28 SHEETS) is a block diagram of an example configuration of FIG. 14, the signal pathway having a multiplexer for simultaneously driving more than one ultrasonic transducer element in the ultrasonic transducer array.
Figure 17:
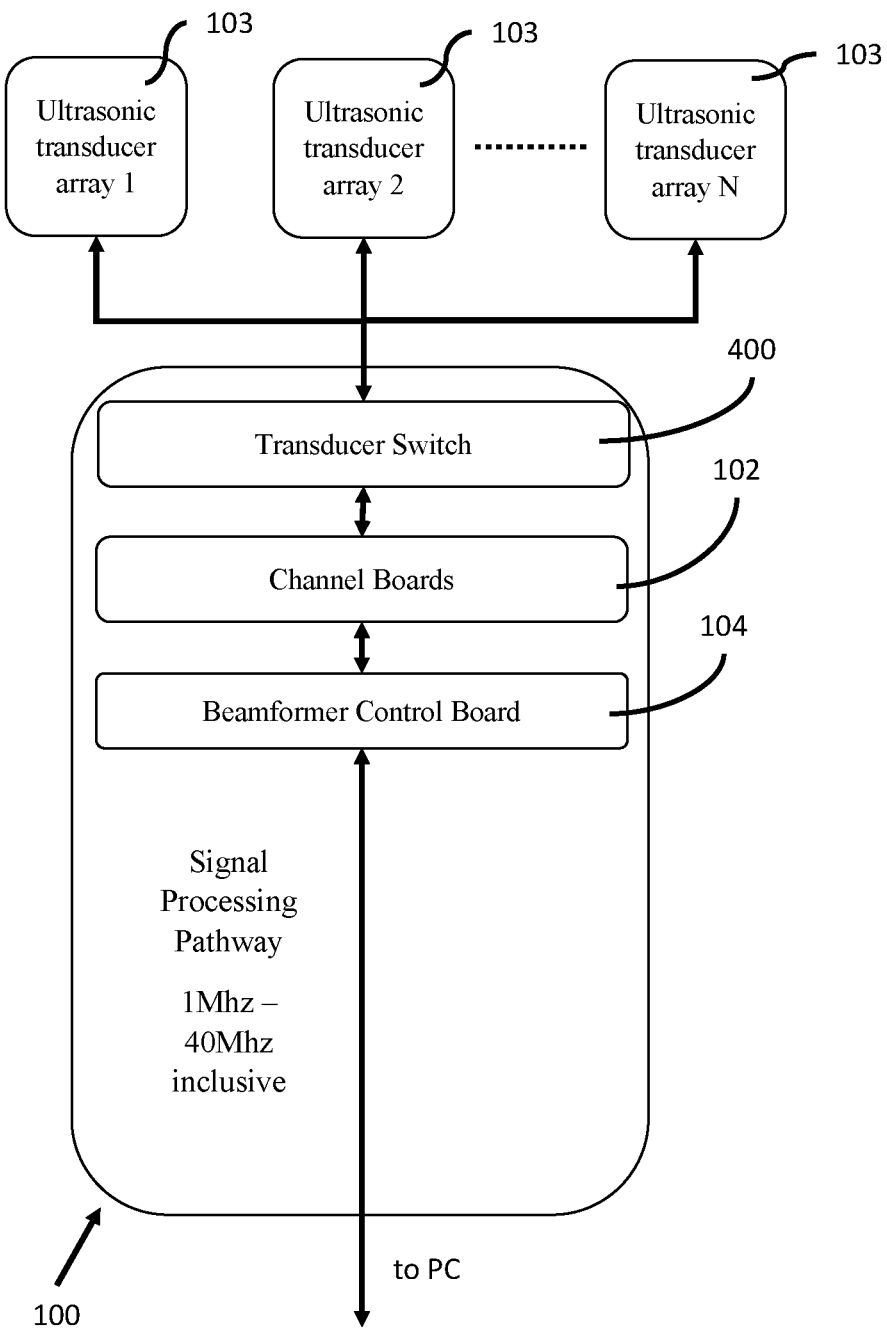
FIG. 17 (SHEET 18 of 28 SHEETS) is a block diagram of an example configuration of FIG. 13, the signal pathway configured to operate with N ultrasonic transducer arrays.
Figure 18:
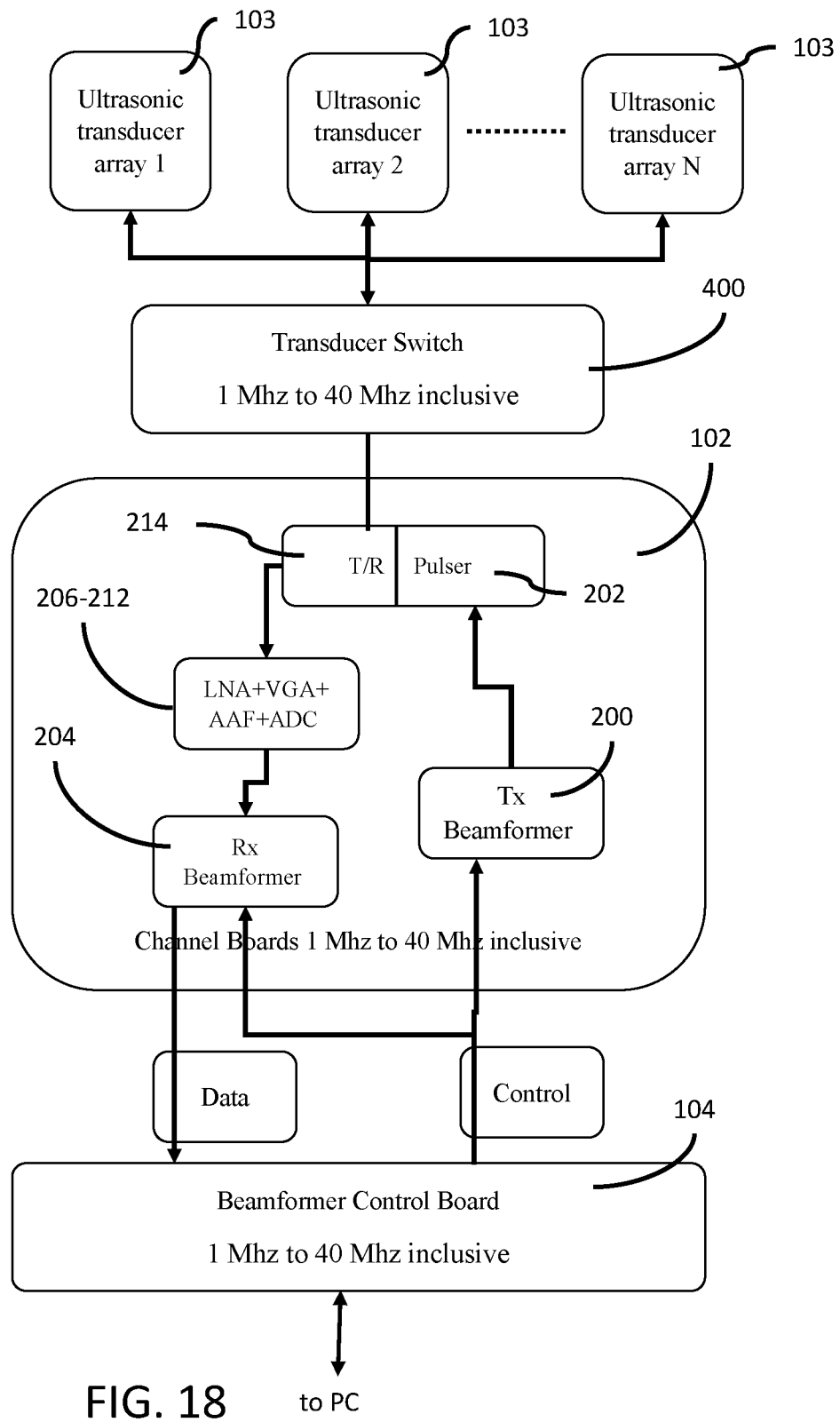
FIG. 18 (SHEET 19 of 28 SHEETS) is a block diagram of an example configuration of FIG. 14, the signal pathway configured to operate with N ultrasonic transducer arrays.
Figure 19:
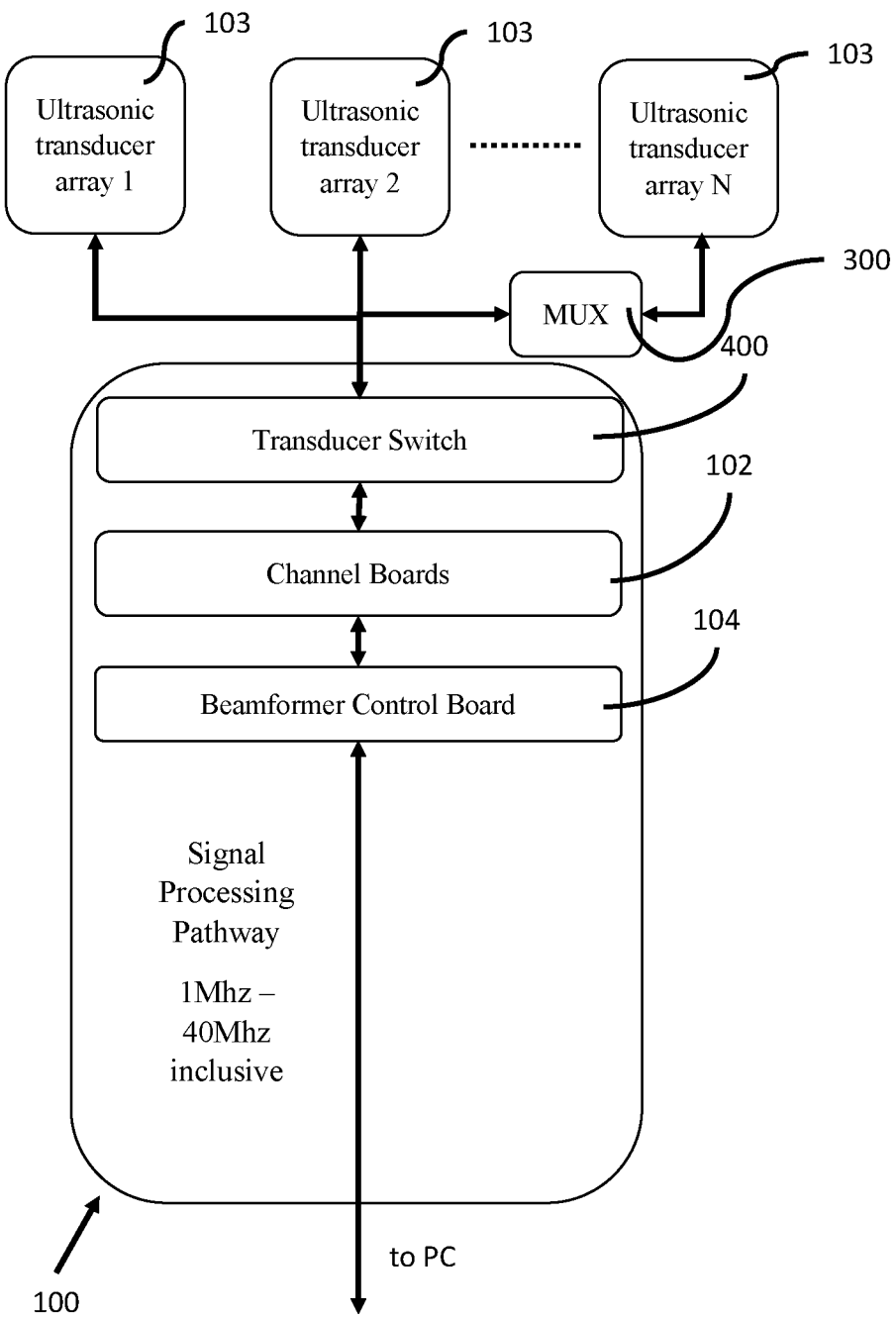
FIG. 19 (SHEET 20 of 28 SHEETS) is a block diagram of an example configuration of FIG. 13 the signal pathway configured to operate with N ultrasonic transducer arrays and the signal pathway having a multiplexer for simultaneously driving more than one ultrasonic transducer element in the ultrasonic transducer array.
Figure 20:
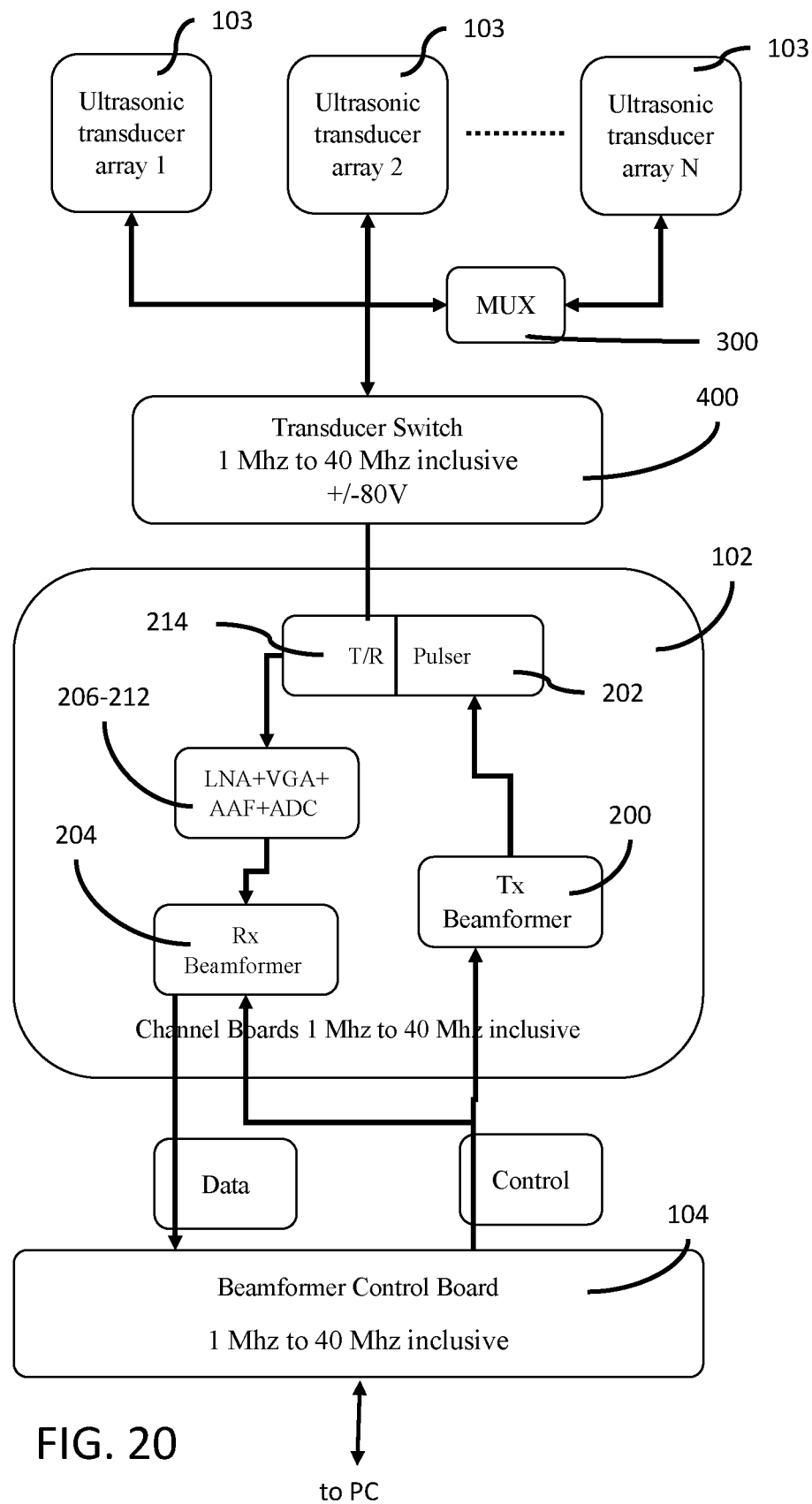
FIG. 20 (SHEET 21 of 28 SHEETS) is a block diagram of an example configuration of FIG. 14 the signal pathway configured to operate with N ultrasonic transducer arrays and the signal pathway having a multiplexer for simultaneously driving more than one ultrasonic transducer element in the ultrasonic transducer array.
Figure 21:
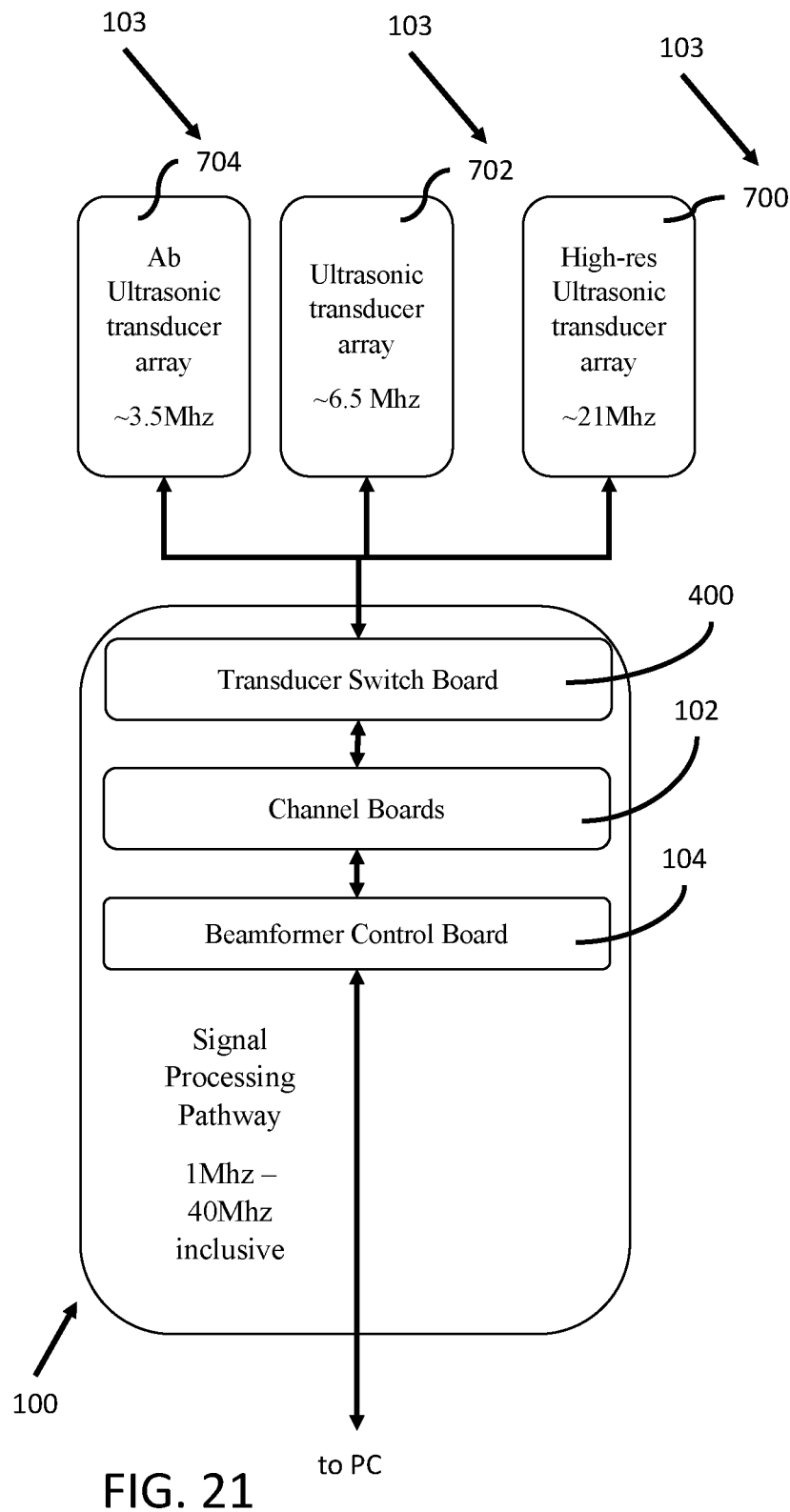
FIG. 21 (SHEET 22 of 28 SHEETS) is a block diagram of an example configuration of FIG. 13, the signal pathway configured to operate with an abdominal (3.5 MHz), a trans-rectal (6.5 MHz), and an ultra-high resolution trans-rectal (21 MHz) ultrasonic transducer arrays.
Figure 22:
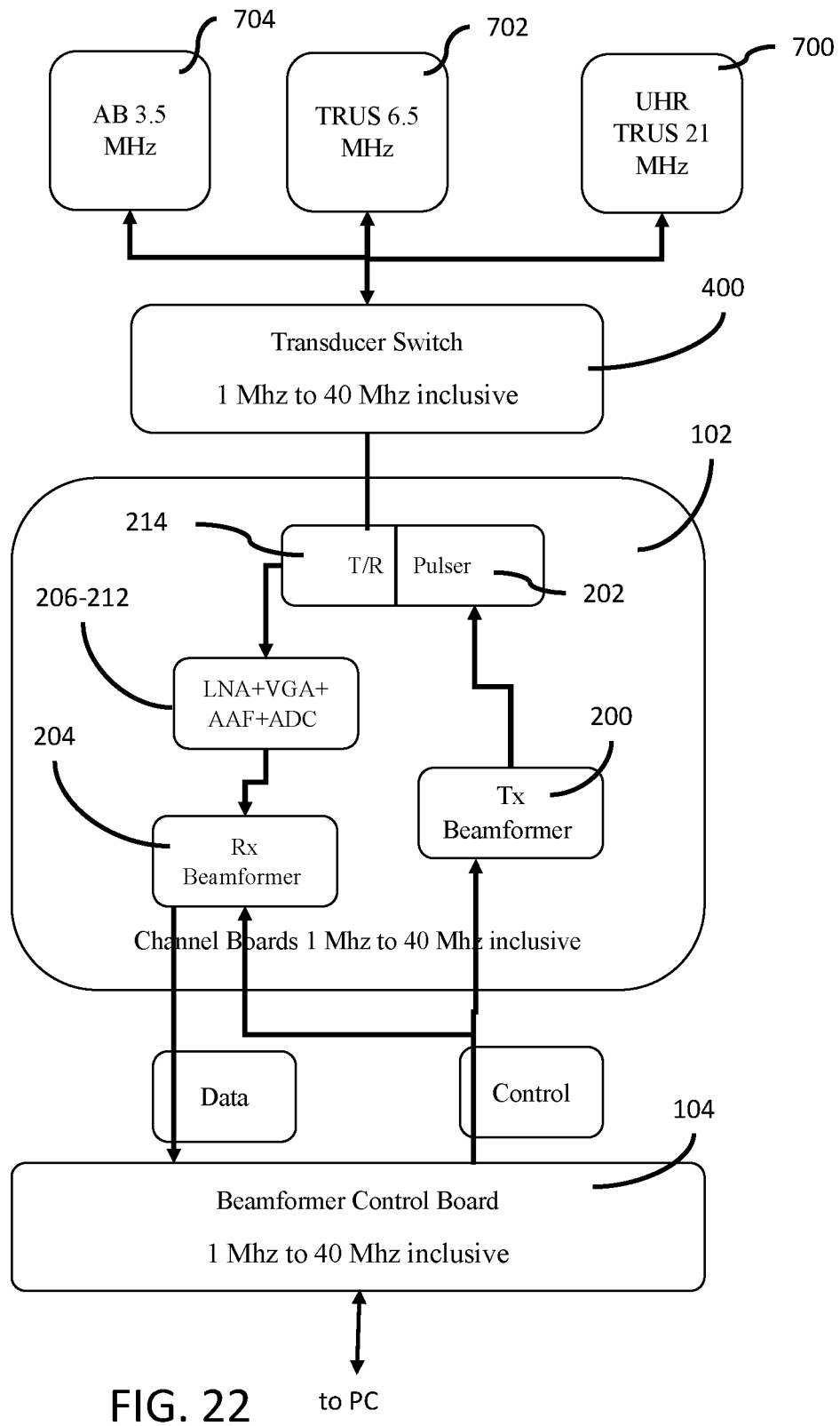
FIG. 22 (SHEET 23 of 28 SHEETS) is a block diagram of an example configuration of FIG. 14, the signal pathway configured to operate with an abdominal (3.5 MHz), a trans-rectal (6.5 MHz), and an ultra-high resolution trans-rectal (21 MHz) ultrasonic transducer arrays.
Figure 23:
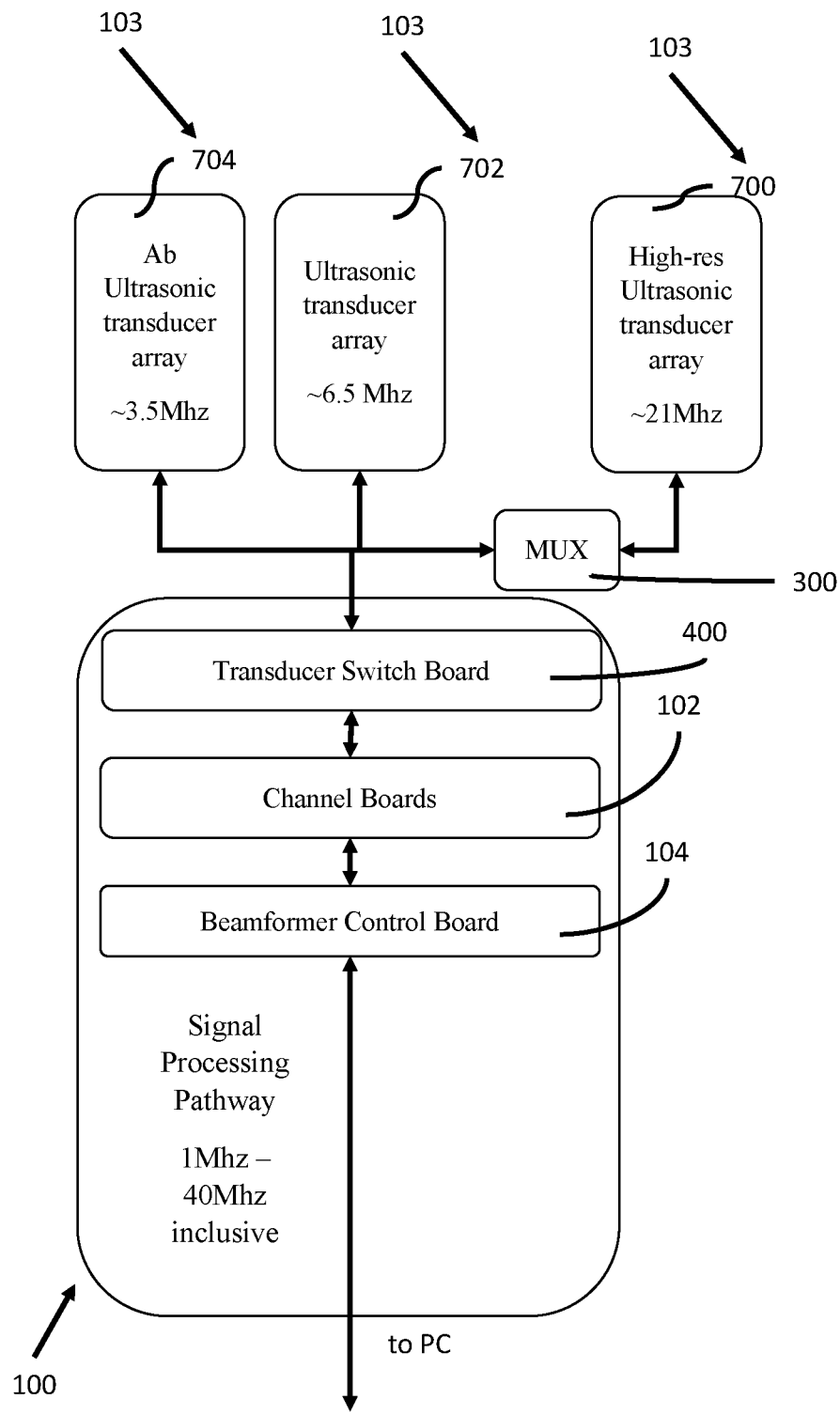
FIG. 23 (SHEET 24 of 28 SHEETS) is a block diagram of an example configuration of FIG. 13, the signal pathway configured to operate with an abdominal (3.5 MHz), a trans-rectal (6.5 MHz), and an ultra-high resolution trans-rectal (21 MHz) ultrasonic transducer arrays, and the signal pathway having a multiplexer for simultaneously driving more than one ultrasonic transducer element in the ultrasonic transducer array.
Figure 24:
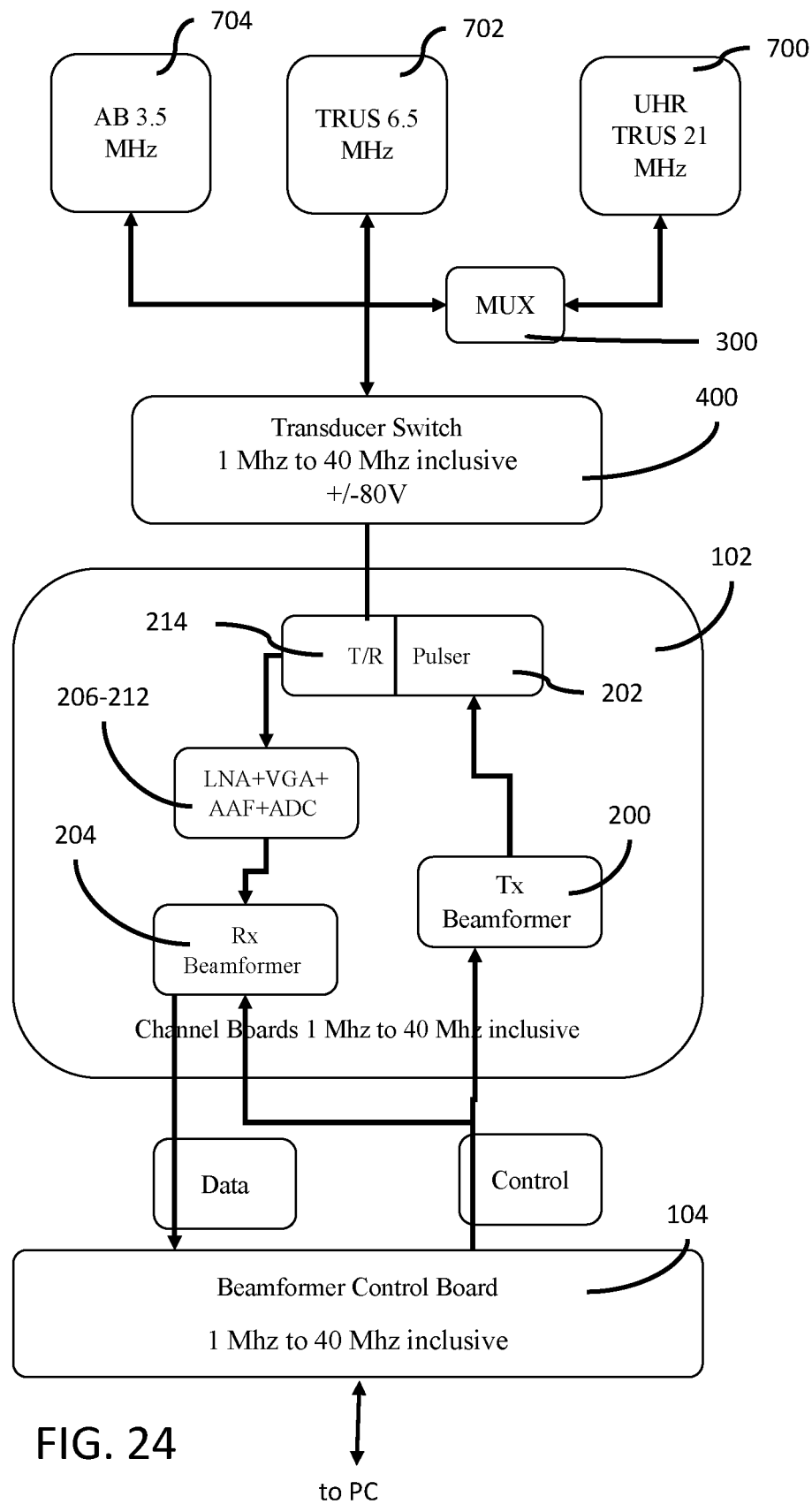
FIG. 24 (SHEET 25 of 28 SHEETS) is a block diagram of an example configuration of FIG. 14, the signal pathway configured to operate with an abdominal (3.5 MHz), a trans-rectal (6.5 MHz), and an ultra-high resolution trans-rectal (21 MHz) ultrasonic transducer arrays, and the signal pathway having a multiplexer for simultaneously driving more than one ultrasonic transducer element in the ultra-high resolution ultrasonic transducer array.

Referring now to FIG. 15 and FIG. 16, a transducer element multiplexer 300 is provided on the signal path 100 in order to mitigate, at least in part, the problem of activating more ultrasonic transducer elements than there are signal processing channels. The transducer element multiplexer 300 has the same role as in FIG. 3 and FIG. 4.

As was previously discussed, the transducer element multiplexer 300 allows more than one ultrasonic transducer element in the ultrasonic transducer element array 103 to be activated for each channel in the signal pathway 100. This allows an increase in the field of view for the ultrasonic transducer array 103 while maintaining the desired resolution.

Referring now to FIG. 17, FIG. 18, FIG. 19, and FIG. 20 in some embodiments the signal processing pathway 100 is operable with more than one ultrasonic transducer array 103. In these embodiments, a transducer switch 400 is provided. The transducer switch 400 is configured to selectably switch between more than one ultrasonic transducer array 103. This role of the transducer switch 400 is the same as was discussed for FIG. 5, FIG. 6, FIG. 7, and FIG. 8.

Referring now to FIG. 21, FIG. 22, FIG. 23, and FIG. 24, these figures depict various signal pathways 100 having combinations of the features described above. It is noted that the combinations are similar to those described in FIG. 9, FIG. 10, FIG. 11, and FIG. 12.

The below data bandwidth requirements do not apply for the non-summed or non-beamformed receive beamformer embodiment.

Figure 25A:
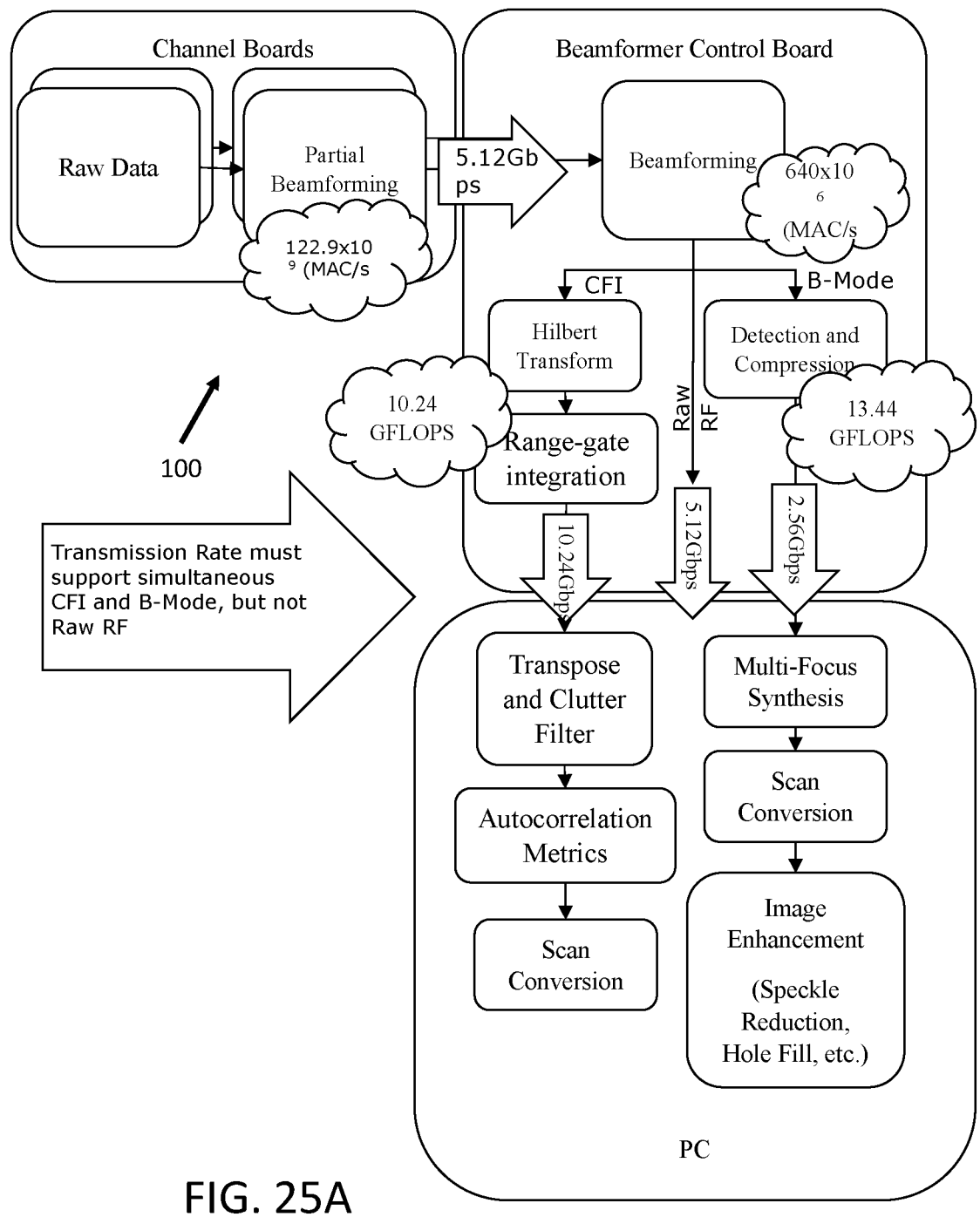
FIG. 25A (SHEET 26 of 28 SHEETS) is a block diagram of an example configuration of a signal pathway and its associated data bandwidth requirements, the data bandwidth requirements between the channel boards, beamformer control boards of the signal processing pathway, and the processing device of an ultrasonic imaging device.

Referring now to FIG. 25A, the data bandwidth requirements for an example signal processing pathway 100 having 128 channels is provided. A skilled person would understand that the data bandwidth requirements for the signal processing pathway 100 will depend on various factors such as, but not limited to, the number of samples taken, the number of signal processing pathway channels, and the amount of beamforming performed prior to transmitting the received data towards the data processor.

In the example provided in FIG. 25A, the data bandwidth requirements between the channel board 102 to the beamformer board 104 is determined as follows:

The number of samples generated for each line is given by:

$$N_{Samples/Line} = \frac{\text{depth}}{\text{speed}} f_s \cdot N_{Aperature}$$

If this value is partially beamformed over the number of channels on the channel board the final number of bits will be:

$$D_{Samples/Line} = \frac{\text{depth}}{\text{speed}} f_s \cdot N_{bits}$$

This data must be transmitted to the beamformer control board in, at worst, the time it takes to acquire the line (depth/speed). Therefore the data transfer rate must be at least:

$$\text{Rate}_{CB \rightarrow BCB} = f_s \cdot N_{bits}$$

Given a sampling rate of 80 MSPS with 16 bit resolution (originally 12 bits, converted to 16 during partial beamforming), the system must support at least 1.28 Gbps. Since we require multi-line beamforming, this rate must be multiplied by $N_{Multi-Lines}=4$ which is the number of simultaneously received lines permitted, for a total of 5.12 Gbps.

It should be noted that the data bandwidth between the beamformer control board and the data processor/PC may be less than the data bandwidth between the beamformer control board and the channel board. This is because the beamformer board can be configured to process, including compressing, the received signal so as to reduce the bandwidth requirements.

Figure 25B:
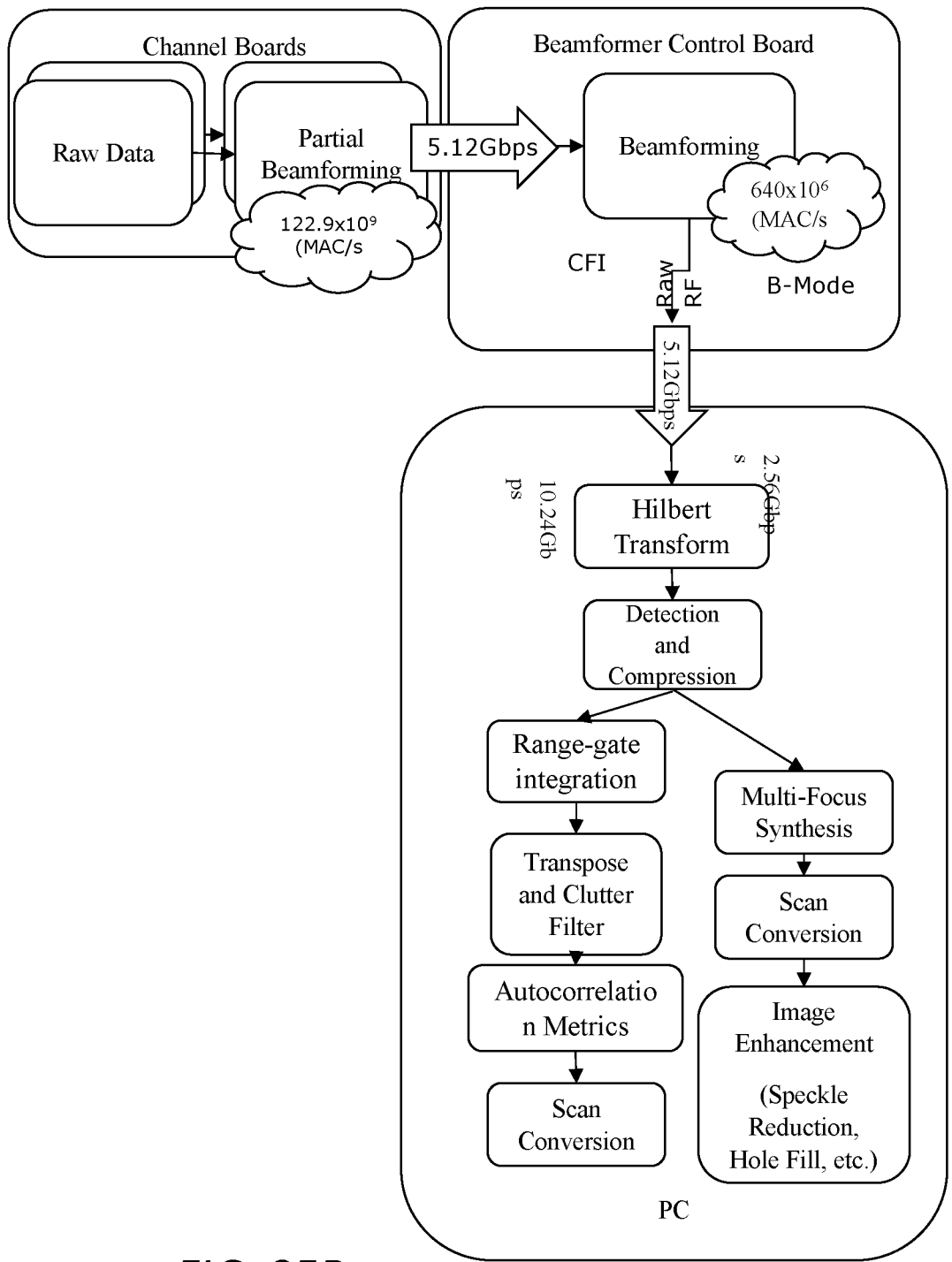
FIG. 25B (SHEET 27 of 28 SHEETS) is a block diagram of an alternate configuration of a signal pathway and its associated data bandwidth requirements, the data bandwidth requirements between the channel boards, beamformer control boards of the signal processing pathway, and the processing device of an ultrasonic imaging device.

Referring now to FIG. 25B, the data bandwidth requirements for an alternate signal processing pathway 100 (as compared to FIG. 25A) having 128 channels is provided. A skilled person would understand that the data bandwidth requirements for the signal processing pathway 100 will depend on various factors such as, but not limited to, the number of samples taken, the number of signal processing pathway channels, and the amount of beamforming performed prior to transmitting the received data towards the data processor.

In this embodiment considerably more of the processing is performed by the data processor/PC when compared to FIG. 25A. In this embodiment the beamformer control board transmits raw data directly to the data processor. The data processor then performs the transformations and/or processing that would have been performed on the beamformer control board in FIG. 25A. Relying on the data processor simplifies the beamformer control board which may translate to cost and/or power savings. Furthermore, upgrading the data processor may result in data processing performance improvements without the need to replace the beamformer control board.

Figure 26:
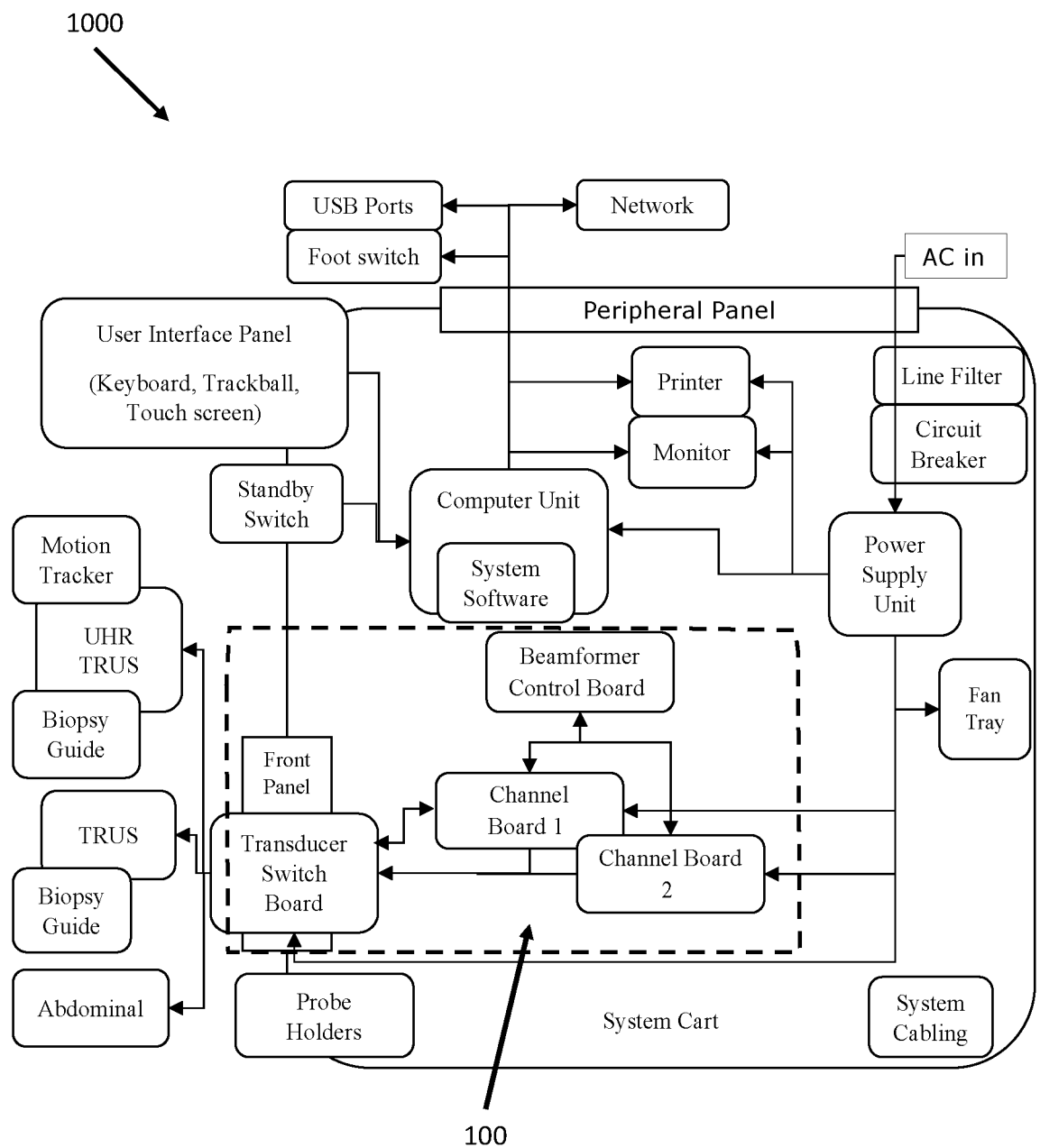
FIG. 26 (SHEET 28 of 28 SHEETS) is a block diagram of an example configuration of the signal processing pathway as used in an ultrasonic imaging device.

Referring now to FIG. 26, an example ultrasound imaging device 1000 having a signal control pathway 100 of the present disclosure is depicted. In this example, the signal control pathway 100 has two channel control boards 103, each having 64 channels (128 channels total). The signal processing pathway 100 is configured to be switchably operable with three ultrasonic transducer arrays—an abdominal transducer array, a trans-rectal ultrasonic transducer array, and an ultra-high resolution ultrasonic transducer array. In this example, the trans-rectal ultrasonic transducer array, and the ultra-high resolution ultrasonic transducer array also have biopsy guides. The ultra-high resolution ultrasonic transducer array also includes a motion tracker to track the motion of the transducer array. A skilled person would understand that other transducer array accessories could be used without departing from the scope of this disclosure.

The signal processing pathway 100 is a part of a larger ultrasound imaging device 1000. The ultrasound imaging device 1000 is configured to acquire and process ultrasonic imaging data from the ultrasonic transducer arrays through the signal processing pathway 100. In this example a computer is configured to allow a user, through the user interface panel, to acquire and process ultrasound imaging data.

It will be appreciated that the signal processing pathway 100 will be a part of a larger ultrasonic imaging device 1000. An example of a method for using an ultrasonic imaging device 1000 having a signal processing pathway 100 as presently disclosed includes, but is not limited to, the following steps:
 a) selecting, via a user interface, switch, or selection device, an ultrasonic transducer array 103 that will be used to scan an object in a human body;
 b) activating, the selected ultrasonic transducer array 103 to obtain data about the object;
 c) processing the data about the object; and
 d) presenting the data in a human-readable format.

It would be understood that other methods for using the ultrasonic imaging device 1000 and the signal processing pathway 100 can be contemplated that would be within the scope of this disclosure. Examples include, but are not limited to, outputting unprocessed data to a second interface, sending the human-readable data to an off-site location, or printing the human-readable data.

In an example, a method of using an ultrasonic imaging device 1000 having the signal processing pathway 100 as presently disclosed is as follows: An ultrasonic imaging device operator selects a low-frequency ultrasonic transducer array (3.5 MHz Abdominal) to scan the abdomen of a subject in order to locate and image the subject's prostate. Once the subject's prostate is located, the trans-rectal ultrasonic transducer array (6.5 MHz TRUS) may be selected to scan the subject's prostate to measure prostate volume and locate zones within the prostate. For instance, a systematic sextant biopsy may be performed using the trans-rectal ultrasonic transducer array (6.5 MHz TRUS).

The ultra-high resolution trans-rectal ultrasonic transducer array (21 MHz) may be selected to locate and identify structures in the prostate that are smaller than 5 mm. In this example, a doctor may guide a needle towards the suspicious area in the prostate in order to obtain a targeted biopsy sample. In some examples, the needle head may also be detected by the ultra-high resolution trans-rectal ultrasonic transducer array (21 MHz). This is useful in helping the person performing the biopsy to guide, at least in part, the needle head towards the suspicious area in the prostate.

The following clauses are offered as further description of the examples of the apparatus. Any one or more of the following clauses may be combinable with any another one or more of the following clauses and/or with any subsection or a portion or portions of any other clause and/or combination and permutation of clauses. Any one of the following clauses may stand on its own merit without having to be combined with any other clause or any portion of any other clause, etc. CLAUSE 1 An apparatus of any clause in this paragraph, further comprising (if so desired) a signal processing pathway 100 for an ultrasonic imaging device 1000, the signal processing pathway 100 comprising: a transmit pathway 106 configured to transmit a transmitted signal to an ultrasonic transducer array 103; a receive pathway 108 configured to receive a received signal from the ultrasonic transducer array 103; and a control pathway 110 for controlling a transmission of the transmitted signal and a reception of the received signal; wherein the transmit pathway, receive pathway, and control pathway are configured to operate in a frequency range of 1 MHz to 40 MHz inclusive and a voltage range of −80V to +80V inclusive. CLAUSE 2 An apparatus of any clause in this paragraph, further comprising (if so desired) the signal processing pathway 100 of claim 1, further comprising: the control pathway 110 comprising: a transmit/receive switch 214 for switching between the transmit pathway and the receive pathway; the transmit pathway 106 comprising: a transmit beamformer 200 for controlling a timing and a shape of the transmitted signal; and a pulser 202 for adjusting a voltage of the transmitted signal; and the receive pathway 108 comprising: a receive beamformer 204 for storing and transferring, at least in part, the received signal; an ADC (analog/digital converter) 206 for converting the received signal, a VGA (variable gain amplifier) 208 for amplifying selected properties of the received signal; an AAF (anti-aliasing filter) 210 for preventing aliasing and for limiting a noise of the received signal; and a LNA (low noise amplifier) 212 for amplifying the received signal; CLAUSE 3 An apparatus of any clause in this paragraph, further comprising (if so desired) the signal processing pathway 100 of any one of claims 1 to 2, further comprising a transducer element multiplexer 300 configured for selecting one or more ultrasonic transducer elements in the ultrasonic transducer array 103 to be driven for each channel in the transmit pathway. CLAUSE 4 An apparatus of any clause in this paragraph, further comprising (if so desired) the signal processing pathway 100 of any one of claims 1 to 3 further comprising: a transducer switch 400 for switching between two or more ultrasonic transducer arrays 103, wherein each of the ultrasonic transducer arrays 103 is configured to operate in a frequency subrange of the signal processing pathway 100. CLAUSE 5 An apparatus of any clause in this paragraph, further comprising (if so desired) the signal processing pathway 100 of any one of claims 1 to 4, wherein, the ultrasonic transducer array 103 has a frequency band centered around any one of 21 MHz (UHR-TRUS) 700, 6.5 MHz (TRUS) 702, and 3.5 MHz (Abdominal) 704. CLAUSE 6 An apparatus of any clause in this paragraph, further comprising (if so desired) the signal processing pathway 100 of any one of claims 1 to 5, wherein, the ultrasonic transducer array 103 has a frequency band configured for scanning a human prostate. CLAUSE 7 An apparatus of any clause in this paragraph, further comprising (if so desired) the signal processing pathway 100 of any one of claims 1 to 6, wherein, the transmit pathway and the receive pathway have 128 channels, each channel being configured to transmit the transmitted signal and to receive the received signal from an ultrasonic transducer element in the ultrasonic transducer array 103. CLAUSE 8 An apparatus of any clause in this paragraph, further comprising (if so desired) the signal processing pathway of any one of claims 1 to 6, wherein, the transmit pathway and the receive pathway have a number of channels, the number of channels being proportional to the highest frequency ultrasonic transducer so as to maintain a resolution operable to scan a human prostate. CLAUSE 9 An apparatus of any clause in this paragraph, further comprising (if so desired) the signal processing pathway 100 of any one of claims 3 to 8, wherein, the transducer element multiplexer 300 is a 4:1 multiplexer so that the ultrasonic transducer array 103 having 512 ultrasonic transducer elements is driven by the transmit pathway, the transmit pathway having 128 channels. CLAUSE 10 An apparatus of any clause in this paragraph, further comprising (if so desired) the signal processing pathway 100 of any one of claims 2 to 8, wherein, the receive beamformer 204 also delays, scales, and sums, at least in part, the received signal. CLAUSE 11 An apparatus of any clause in this paragraph, further comprising (if so desired) a signal processing pathway 100 for an ultrasonic imaging device 1000, the signal processing pathway 100 comprising: a channel board 103 configured to transmit a transmitted signal to, and, to receive a received signal from an ultrasonic transducer array 103; and a beamformer control board 104 configured to control the channel board 103; wherein, the channel board 103 and the beamformer control board 104 are configured to operate in a frequency range of 1 MHz to 40 MHz inclusive and a voltage range of −80V to +80V inclusive. CLAUSE 12 An apparatus of any clause in this paragraph, further comprising (if so desired) the signal processing pathway 100 of claim 11, wherein: the channel board 103 comprises: a transmit/receive switch 214 for switching between the transmit pathway and the receive pathway; a transmit beamformer 200 for controlling a timing and a shape of the transmitted signal; a pulser 202 for adjusting a voltage of the transmitted signal; a receive beamformer 204 for storing and transferring, at least in part, the received signal; an ADC (analog/digital converter) 206 for converting the received signal; a VGA (variable gain amplifier) 208 for amplifying selected properties of the received signal; an AAF (anti-aliasing filter) 210 for preventing aliasing and for limiting a noise of the received signal; and a LNA (low noise amplifier) 212 for amplifying the received signal. CLAUSE 13 An apparatus of any clause in this paragraph, further comprising (if so desired) the signal processing pathway 100 of any one of claims 11 to 12, further comprising: a transducer element multiplexer 300 configured for selecting one or more ultrasonic transducer elements in the ultrasonic transducer array 103 to be driven for each channel in the transmit pathway. CLAUSE 14 An apparatus of any clause in this paragraph, further comprising (if so desired) the signal processing pathway 100 of any one of claims 11 to 13, further comprising: a transducer switch 400 for switching between two or more ultrasonic transducer arrays 103, wherein each of the ultrasonic transducer arrays 103 is configured to operate in a frequency subrange of the signal processing pathway 100. CLAUSE 15 An apparatus of any clause in this paragraph, further comprising (if so desired) the signal processing pathway 100 of any one of claims 11 to 14, wherein, the ultrasonic transducer array 103 has a frequency band centered around of any one of 21 MHz (UHR-TRUS) 700, 6.5 MHz (TRUS) 702, and 3.5 MHz (Abdominal) 704. CLAUSE 16 An apparatus of any clause in this paragraph, further comprising (if so desired) the signal processing pathway 100 of any one of claims 11 to 15, wherein, the ultrasonic transducer array 103 has a frequency band configured for scanning a human prostate. CLAUSE 17 An apparatus of any clause in this paragraph, further comprising (if so desired) the signal processing pathway 100 of any one of claims 11 to 16, the transmit pathway and the receive pathway have 128 channels, each channel being configured to transmit the transmitted signal and to receive the received signal from an ultrasonic transducer element in the ultrasonic transducer array 103. CLAUSE 18 An apparatus of any clause in this paragraph, further comprising (if so desired) the signal processing pathway of any one of claims 11 to 17, wherein, the transmit pathway and the receive pathway have a number of channels, the number of channels being proportional to the highest frequency ultrasonic transducer so as to maintain a resolution operable to scan a human prostate. CLAUSE 19 An apparatus of any clause in this paragraph, further comprising (if so desired) the signal processing pathway 100 of claims 13 to 18, wherein, the transducer element multiplexer 300 is a 4:1 multiplexer so that the ultrasonic transducer array 103 having 512 ultrasonic transducer elements is driven by the transmit pathway, the transmit pathway having 128 channels. CLAUSE 20 An apparatus of any clause in this paragraph, further comprising (if so desired) the signal processing pathway 100 of any one of claims 11 to 19, wherein, the receive beamformer 204 also delays, scales, and sums, at least in part, the received signal. CLAUSE 21 An apparatus of any clause in this paragraph, further comprising (if so desired) the signal processing pathway 100 of any one of claims 1 to 20, wherein, the signal processing pathway 100 has a data bandwidth configured to allow for high speed transfer of data from the channel board 102 to a processing device. CLAUSE 22 An apparatus of any clause in this paragraph, further comprising (if so desired) the signal processing pathway 100 of any one of claims 1 to 21, wherein, the signal processing pathway is configured on a daughterboard for an ultrasonic imaging device. CLAUSE 23 An apparatus of any clause in this paragraph, further comprising (if so desired) the signal processing pathway 100 of any one of claims 1 to 21, wherein, the signal processing pathway is configured on an expansion board for a PC. CLAUSE 24 An ultrasonic imaging device 1000 having the features of any of the clauses in this paragraph. CLAUSE 25 A method for using the ultrasonic imaging device 100 having the features of any of the clauses in this paragraph. CLAUSE 26 A method for operating an ultrasonic imaging device, comprising: providing a transmit pathway 106 for transmitting a transmitted signal to an ultrasonic transducer array 103; providing a receive pathway 108 for receiving a received signal from the ultrasonic transducer array 103; providing a control pathway 110 for controlling a transmission of the transmitted signal and a reception of the received signal; and configuring the transmit pathway, the receive pathway, and the control pathway to operate in a frequency range of 1 MHz to 40 MHz inclusive and a voltage range of −80V to +80V inclusive.

It will be appreciated that the description identifies and describes options and variations of the signal processing pathway 100, regardless of whether the description identifies the options and/or variations of the signal processing pathway 100 by way of explicit terms and/or non-explicit terms. Other options for the signal processing pathway 100 as identified in this paragraph may include any combination and/or permutation of the technical features (assemblies, components, items, devices, etc.) as identified in the detailed description, as may be required and/or desired to suit a particular technical purpose and/or technical function. It will be appreciated, that where possible, any one or more of the technical features and/or any one or more sections of the technical features of the signal processing pathway 100 may be combined with any other one or more of the technical features and/or any other one or more sections of the technical features of the bread product 100 in any combination and/or permutation. Any one or more of the technical features and/or any one or more sections of the technical features of the signal processing pathway 100 may stand on its own merit without having to be combined with another technical feature. It will be appreciated that persons skilled in the art would know that technical features of each embodiment may be deployed (where possible) in other embodiments even if not expressly stated as such above. It will be appreciated that persons skilled in the art would know that other options would be possible for the configuration of the components of the signal processing pathway 100 (if so desired) to adjust to manufacturing requirements and still remain within the scope of the invention as described in at least one or more of the claims. This written description uses examples to disclose the invention, including the best mode, and also to enable any person skilled in the art to make and use the invention. The patentable scope of the invention is defined by the claims, and may include other examples that occur to those skilled in the art. Such other examples are within the scope of the claims if they have structural elements that do not differ from the literal language of the claims, or if they include equivalent structural elements with insubstantial differences from the literal language of the claims. It may be appreciated that the assemblies and modules described above may be connected with each other as required to perform desired functions and tasks within the scope of persons of skill in the art to make such combinations and permutations without having to describe each and every one in explicit terms. There is no particular assembly or component that may be superior to any of the equivalents available to the person skilled in the art. There is no particular mode of practicing the disclosed subject matter that is superior to others, so long as the functions may be performed. It is believed that all the crucial aspects of the disclosed subject matter have been provided in this document. It is understood that the scope of the present invention is limited to the scope provided by the independent claim(s), and it is also understood that the scope of the present invention is not limited to: (i) the dependent claims, (ii) the detailed description of the non-limiting embodiments, (iii) the summary, (iv) the abstract, and/or (v) the description provided outside of this document (that is, outside of the instant application as filed, as prosecuted, and/or as granted). It is understood, for this document, that the phrase "includes" is equivalent to the word "comprising." The foregoing has outlined the non-limiting embodiments (examples). The description is made for particular non-limiting embodiments (examples). It is understood that the non-limiting embodiments are merely illustrative as examples.

What is claimed is:

1. A signal processing pathway for an ultrasonic imaging device, the signal processing pathway comprising:
   a channel board configured to transmit a transmitted signal to an ultrasonic transducer array, and further configured to receive a received signal from the ultrasonic transducer array further comprises:
   a transmit/receive switch for switching between a transmit pathway and a receive pathway;
   a transmit beamformer situated in the transmit pathway for controlling a timing and a shape of the transmitted signal;
   a pulser situated in the transmit pathway between the transmit beamformer and the transmit/receive switch for adjusting a voltage of the transmitted signal;
   a receive beamformer situated in the receive pathway for storing and transferring, at least in part, the received signal;
   an ADC (analog/digital converter) situated in the receive pathway between the transmit/receive switch and the receive beamformer for converting the received signal;
   a VGA (variable gain amplifier) situated in the receive pathway between the transmit/receive switch and the receive beamformer for amplifying selected properties of the received signal;
   an AAF (anti-aliasing filter) situated in the receive pathway between the transmit/receive switch and the receive beamformer for preventing aliasing and for limiting a noise of the received signal; and
   a LNA (low noise amplifier) situated in the receive pathway between the transmit/receive switch and the receive beamformer for amplifying the received signal; and
   a beamformer control board configured to control the channel board;
   wherein, the channel board and the beamformer control form the receive pathway and the transmit pathway that each have a bandwidth across a frequency range of 1 MHz to 40 MHz inclusive and for voltages within a range of −80V to +80V inclusive, the received signal traverses the receive pathway and the transmitted signal traverses the transmit pathway.

2. The signal processing pathway of claim 1, further comprising: a transducer element multiplexer configured for selecting one or more ultrasonic transducer elements in the ultrasonic transducer array to be driven for each channel in the transmit pathway.

3. The signal processing pathway of claim 2, the transmit pathway and the receive pathway have 128 channels, each channel being configured to transmit the transmitted signal and to receive the received signal from an ultrasonic transducer element in the ultrasonic transducer array.

4. The signal processing pathway of claim 2, wherein, the transmit pathway has a first number of channels and the receive pathway has a second number of channels, the first number of channels and the second number of channels being proportional to the ultrasonic transducer in the ultrasonic array that has the highest transmit frequency so as to maintain a resolution operable to scan a human prostate.

5. The signal processing pathway of claim 4, wherein, the transducer element multiplexer is a 4:1 multiplexer so that the ultrasonic transducer array having ultrasonic transducer elements is driven by the transmit pathway, the transmit pathway having 128 channels.

6. The signal processing pathway of claim 5, further comprising:
   a transducer switch for switching between two or more ultrasonic transducer arrays, wherein each of the ultrasonic transducer arrays is configured to operate in a frequency subrange of the signal processing pathway.

7. The signal processing pathway of claim 6, wherein, there are three ultrasonic transducer arrays having a frequency band centered around 21 MHz, 6.5 MHz, and 3.5 MHz.

8. The signal processing pathway of claim 7, wherein, the ultrasonic transducer array has a frequency band configured for scanning a human prostate.

9. The signal processing pathway of claim 8, wherein, the signal processing pathway has a data bandwidth configured to allow for transfer of data from the channel board to a processing device.

10. The signal processing pathway of claim 9, wherein, the signal processing pathway is configured on a daughterboard for an ultrasonic imaging device.

11. The signal processing pathway of claim 6, further comprising a transducer switch configured as a hot-swap mechanism that enables the two or more transducer arrays to be used in the same signal processing pathway, wherein the transducer switch initializes a given ultrasonic transducer array for use in the ultrasonic imaging system.

12. The signal processing pathway of claim 6, wherein the ultrasonic imaging device comprises a control pathway configured to select the ultrasonic transducer array from the two or more transducer arrays based on parameters characterizing dimensions of an object to be scanned.

13. The signal processing pathway of claim 1, wherein the ultrasonic transducer array is capable of transmitting and receiving signals in the entirety of the frequency and voltage ranges of the signal processing pathway.

14. The signal processing pathway of claim 1, wherein the ultrasonic imaging device generates a warning responsive to detecting that the ultrasonic transducer array for use in the ultrasonic imaging system uses a frequency and/or voltage outside the frequency and/or voltage ranges of the signal processing pathway.

15. The signal processing pathway of claim 1, the beamformer control board is configured to compress the received signal to compress data communicated along the signal processing pathway.

* * * * *